United States Patent
Kwong et al.

(10) Patent No.: US 11,802,303 B2
(45) Date of Patent: Oct. 31, 2023

(54) METHODS FOR MULTIPLEXED CELL ISOLATION USING DNA GATES

(71) Applicant: Georgia Tech Research Corporation, Atlanta, GA (US)

(72) Inventors: Gabriel A. Kwong, Atlanta, GA (US); Shreyas N. Dahotre, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 64 days.

(21) Appl. No.: 16/967,556

(22) PCT Filed: Feb. 7, 2019

(86) PCT No.: PCT/US2019/017066
§ 371 (c)(1),
(2) Date: Aug. 5, 2020

(87) PCT Pub. No.: WO2019/157191
PCT Pub. Date: Aug. 15, 2019

(65) Prior Publication Data
US 2021/0087605 A1   Mar. 25, 2021

Related U.S. Application Data

(60) Provisional application No. 62/627,441, filed on Feb. 7, 2018.

(51) Int. Cl.
C07H 21/02 (2006.01)
C12Q 1/6804 (2018.01)
C12Q 1/6876 (2018.01)
C12Q 1/6886 (2018.01)

(52) U.S. Cl.
CPC ......... *C12Q 1/6804* (2013.01); *C12Q 1/6876* (2013.01); *C12Q 1/6886* (2013.01)

(58) Field of Classification Search
USPC .......... 435/6.1, 6.11, 7.1, 91.1; 436/94, 501; 536/23.1, 24.3, 24.33; 530/300, 350
See application file for complete search history.

(56) References Cited

U.S. PATENT DOCUMENTS

2010/0248242 A1* 9/2010 Gumbrecht .......... C12Q 1/6825
435/6.12
2013/0344508 A1  12/2013  Schwartz et al.
(Continued)

FOREIGN PATENT DOCUMENTS

WO   2019/157191 A1   8/2019

OTHER PUBLICATIONS

Christine E. Probst et al: "Rapid Multitarget Immunomagnetic Separation through Programmable DNA Linker Displacement" Journal of the American Chemical Society, vol. 133, No. 43, Nov. 2, 2011, pp. 17126-17129.
(Continued)

*Primary Examiner* — Frank W Lu
(74) *Attorney, Agent, or Firm* — Meunier Carlin & Curfman LLC

(57) ABSTRACT

Systems and methods for multiplexed cell sorting are provided herein. The disclosed cell sorting system is referred to as DNA gated sorting (DGS). An exemplary system provides a set of orthogonal sorting probes and release probes for sorting cells of one or more different cell types from a biological specimen.

14 Claims, 18 Drawing Sheets
Specification includes a Sequence Listing.

(56) References Cited

U.S. PATENT DOCUMENTS

2014/0100131 A1     4/2014    Gao et al.
2019/0153515 A1*   5/2019    Chen ..................... C40B 50/14

OTHER PUBLICATIONS

Shreyas N. Dahotre et al: "Individually addressable and dynamic DNA gates for multiplexed cell sorting" Proceedings of the National Academy of Sciences of the United States of America, vol. 115, No. 17, Apr. 9, 2018, pp. 4357-4362.

Wu Wei et al: "Strand displacement amplification for ultrasensitive detection of human pluripotent stem cells" Analytica Chimica Acta, Elsevier, Amsterdam, NL, vol. 881, Apr. 3, 2015, pp. 124-130.

International Preliminary Report on Patentability received for PCT Patent Application No. PCT/US2019/017066, dated Aug. 20, 2020, 10 pages.

International Search Report and Written Opinion received for PCT Patent Application No. PCT/US19/017066, dated Jun. 4, 2019, 16 pages.

* cited by examiner

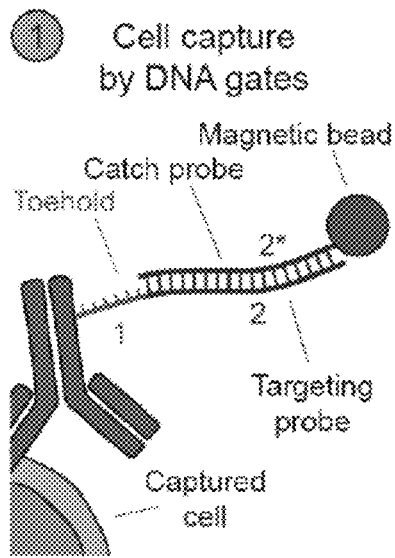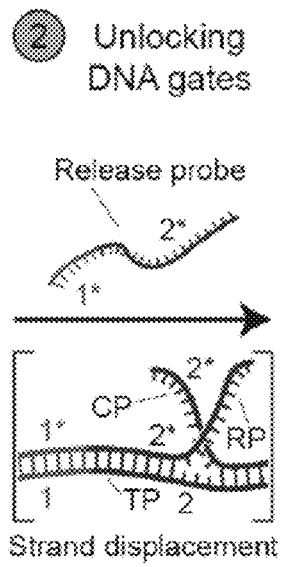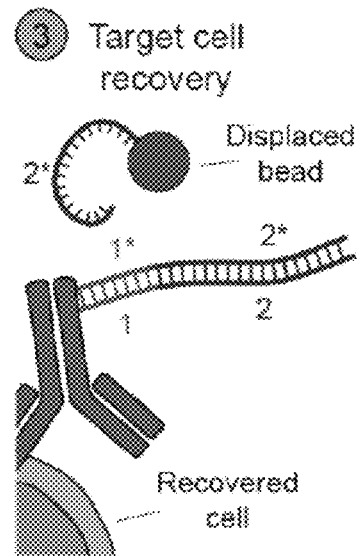
FIGURE 1A    FIGURE 1B    FIGURE 1C
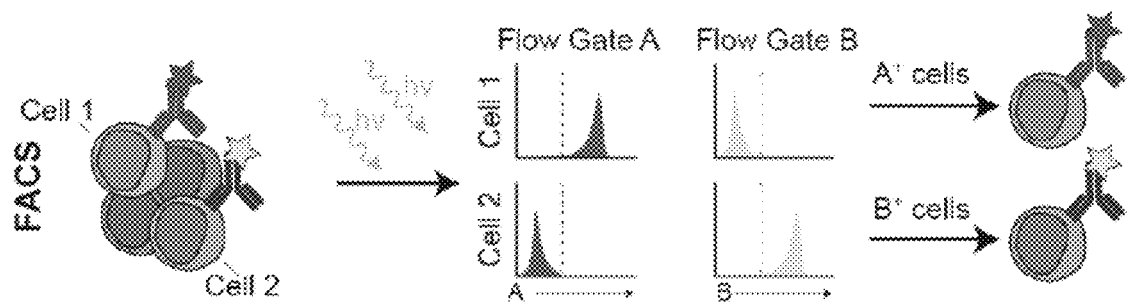
FIGURE 1D
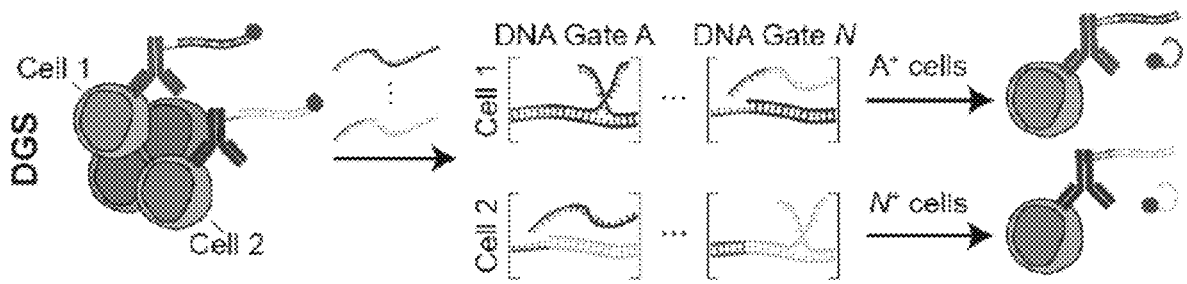
FIGURE 1E

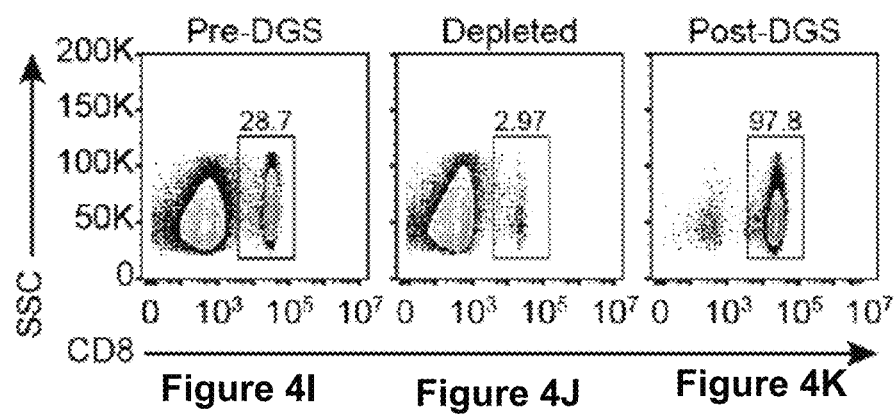
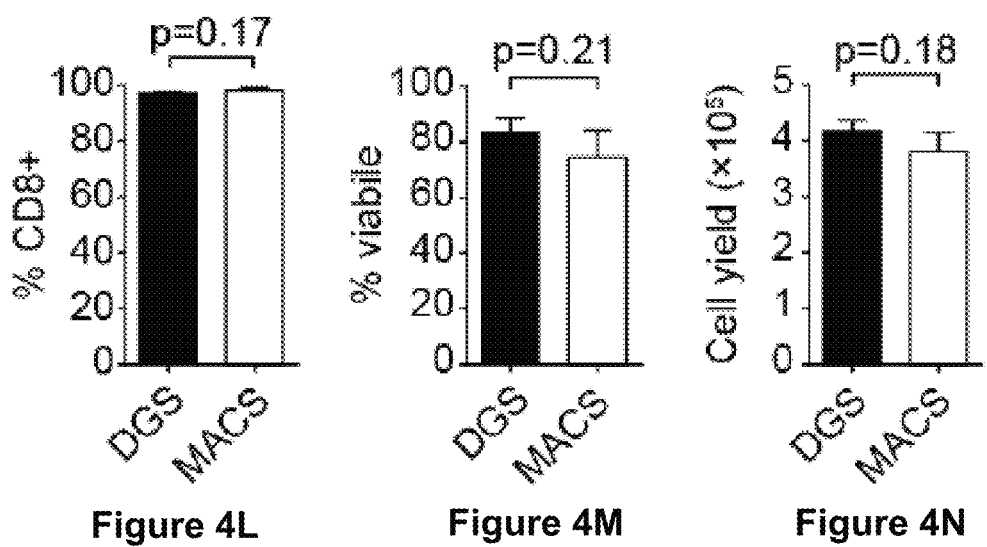

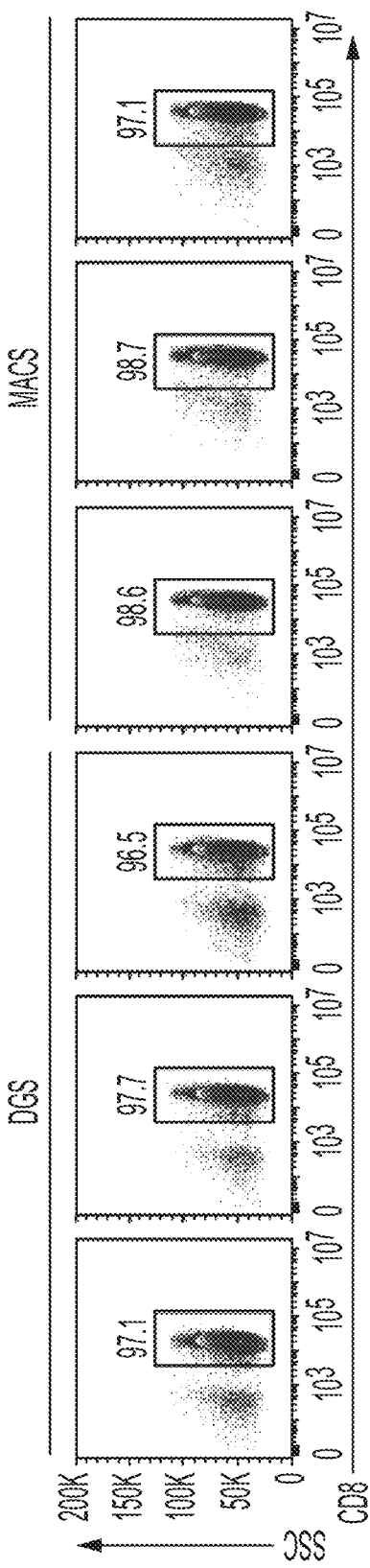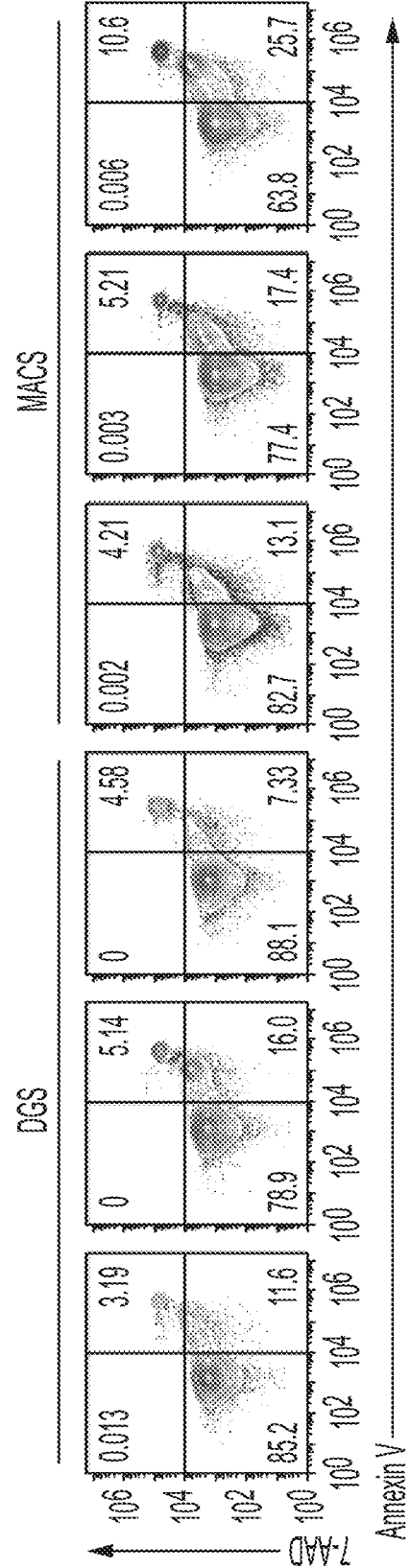

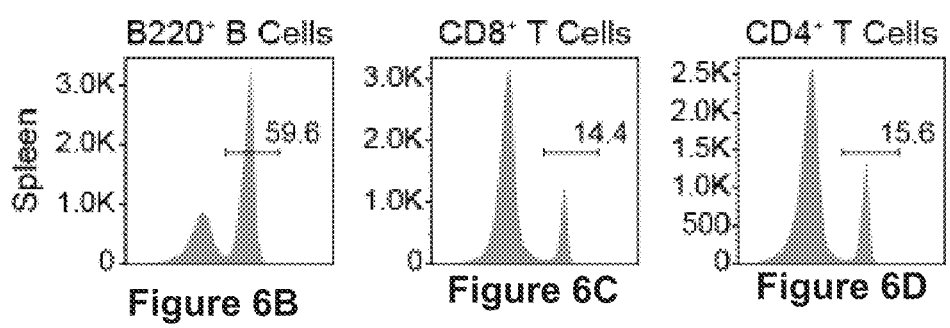
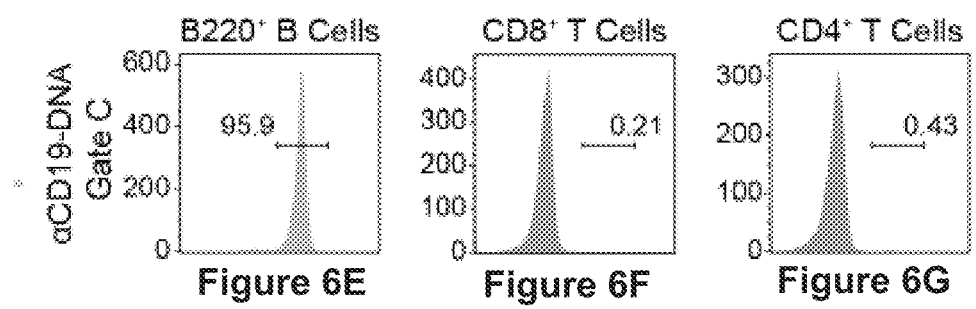
Figure 6B  Figure 6C  Figure 6D
Figure 6E  Figure 6F  Figure 6G

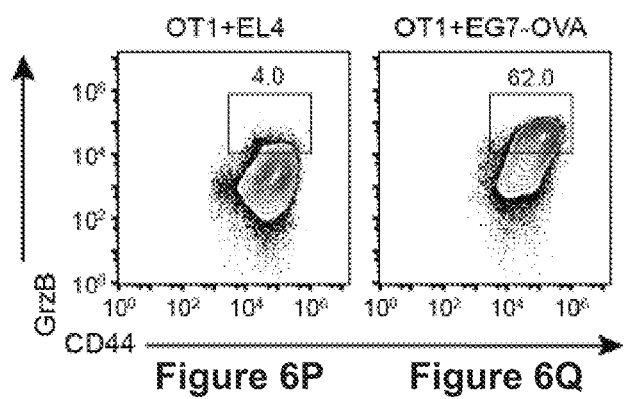

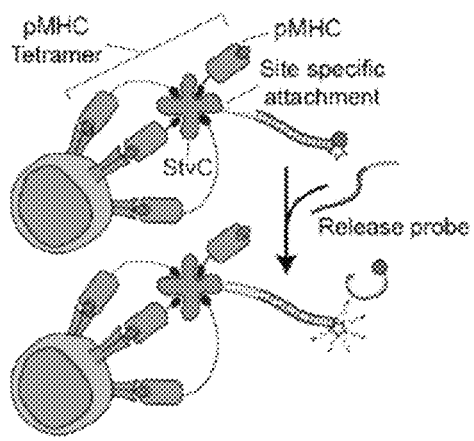
Figure 9A
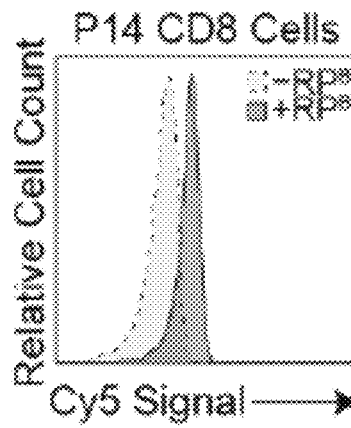 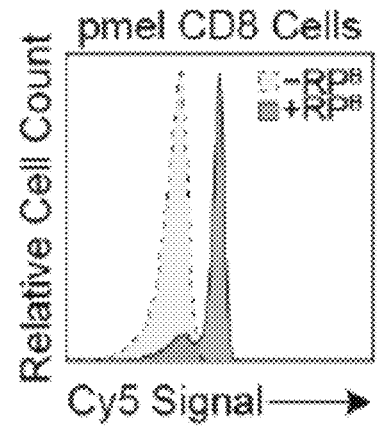
Figure 9B Figure 9C
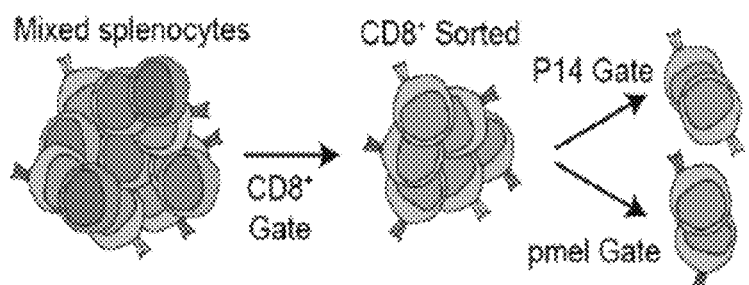
Figure 9D
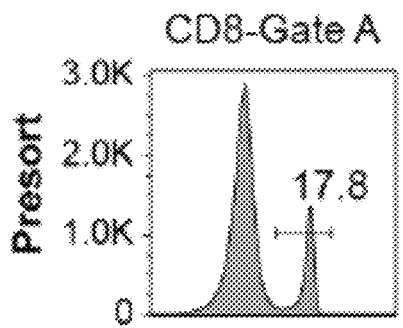 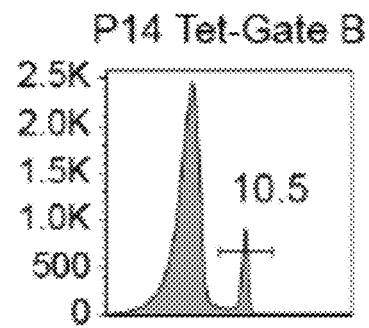 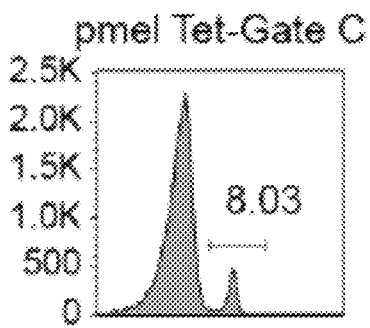
Figure 9E Figure 9F Figure 9G

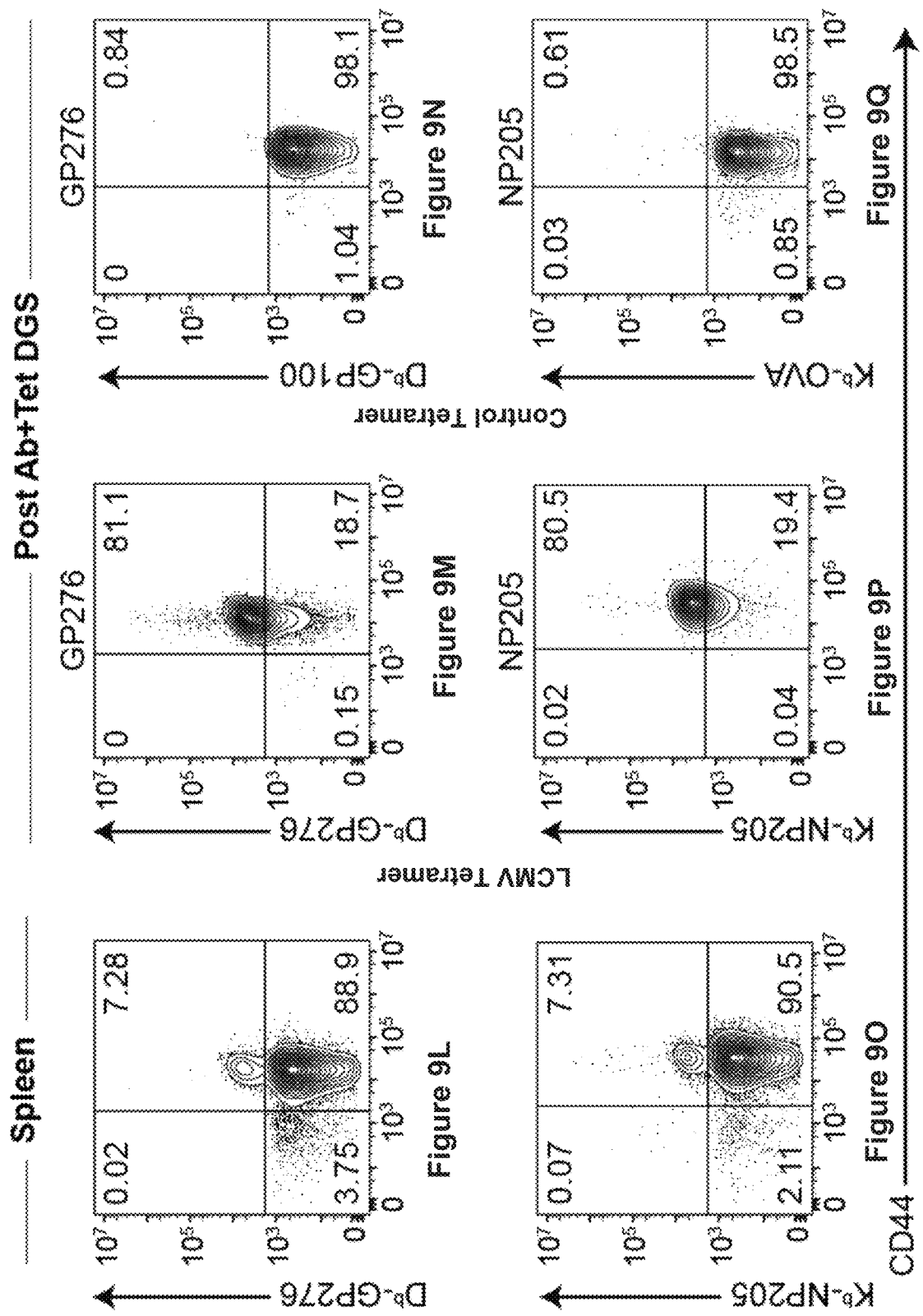

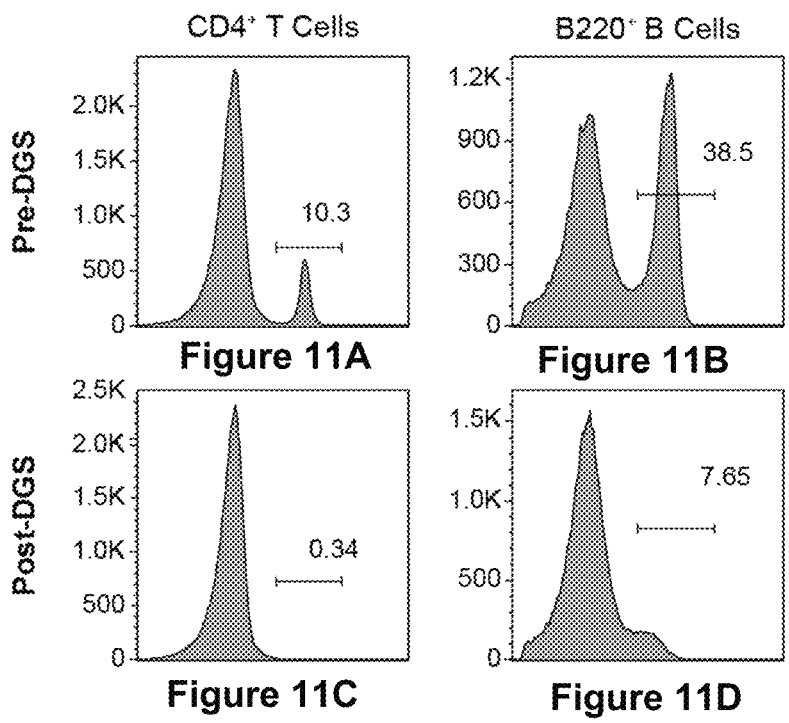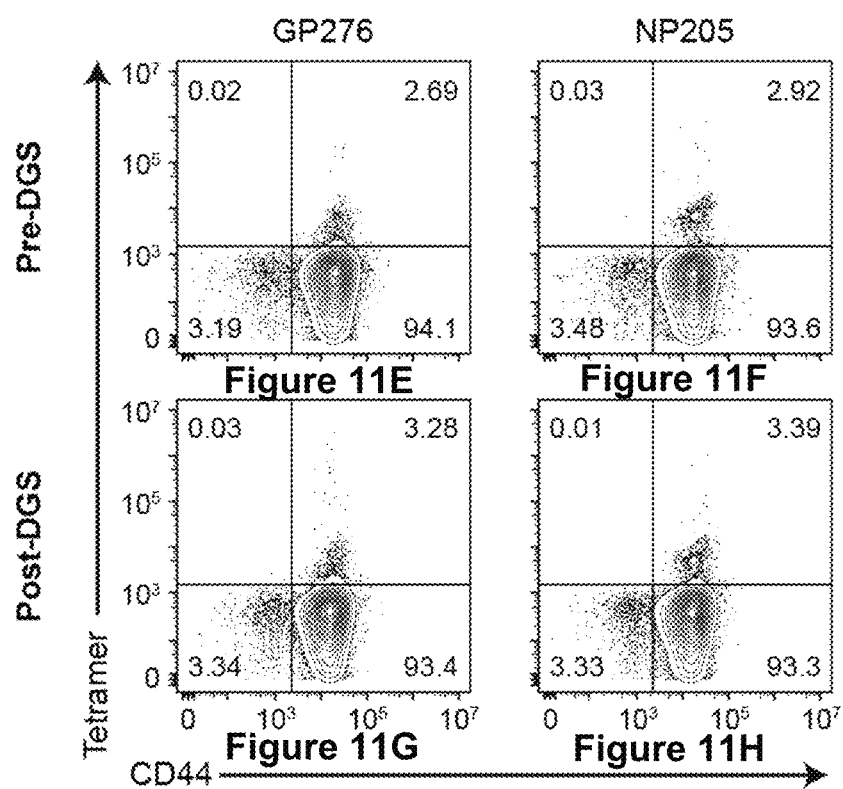

```
                              SEQUENCE LISTING

<160> NUMBER OF SEQ ID NOS: 90

<210> SEQ ID NO 1
<211> LENGTH: 26
<212> TYPE: DNA
<213> ORGANISM: Artificial Sequence
<220> FEATURE:
<223> OTHER INFORMATION: Synthetic

<400> SEQUENCE: 1
ggaacttaac tgggcgcacg atctat                                           26

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
atagatcgtg cgcccagtta                                                  20

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
atagatcgtg cgcccagtta agttcc                                           26

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
gtctcagtct cagtggcgta ataacc                                           26

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ggttattacg ccactgagac                                                  20

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
```

```
ggttattacg ccactgagac tgagac                                         26

<210> SEQ ID NO 7
<211> LENGTH: 26
<212> TYPE: DNA
<213> ORGANISM: Artificial Sequence
<220> FEATURE:
<223> OTHER INFORMATION: Synthetic

<400> SEQUENCE: 7
ggtcatgggg ctataacaac gtctct                                         26

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
agagacgttg ttatagcccc                                                20

<210> SEQ ID NO 9
<211> LENGTH: 26
<212> TYPE: DNA
<213> ORGANISM: Artificial Sequence
<220> FEATURE:
<223> OTHER INFORMATION: Synthetic

<400> SEQUENCE: 9
agagacgttg ttatagcccc atgacc                                         26

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
ggaacttaac tgggcgcacg atctat                                         26

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
aaaaaaaaaa atagatcgtg cgcccagtta                                     30

<210> SEQ ID NO 12
<211> LENGTH: 26
<212> TYPE: DNA
<213> ORGANISM: Artificial Sequence
<220> FEATURE:
<223> OTHER INFORMATION: Synthetic

<400> SEQUENCE: 12
atagatcgtg cgcccagtta agttcc                                         26

<210> SEQ ID NO 13
<211> LENGTH: 26
<212> TYPE: DNA
<213> ORGANISM: Artificial Sequence
```

<220> FEATURE:
<223> OTHER INFORMATION: Synthetic

<400> SEQUENCE: 13
gtctcagtct cagtggcgta ataacc    26

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
aaaaaaaaaa ggttattacg ccactgagac    30

<210> SEQ ID NO 15
<211> LENGTH: 26
<212> TYPE: DNA
<213> ORGANISM: Artificial Sequence
<220> FEATURE:
<223> OTHER INFORMATION: Synthetic

<400> SEQUENCE: 15
ggttattacg ccactgagac tgagac    26

<210> SEQ ID NO 16
<211> LENGTH: 26
<212> TYPE: DNA
<213> ORGANISM: Artificial Sequence
<220> FEATURE:
<223> OTHER INFORMATION: Synthetic

<400> SEQUENCE: 16
ggtcatgggg ctataacaac gtctct    26

<210> SEQ ID NO 17
<211> LENGTH: 30
<212> TYPE: DNA
<213> ORGANISM: Artificial Sequence
<220> FEATURE:
<223> OTHER INFORMATION: Synthetic

<400> SEQUENCE: 17
aaaaaaaaaa agagacgttg ttatagcccc    30

<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
agagacgttg ttatagcccc atgacc    26

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
gagttggaga gttgtgaggg agtatg    26

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
aaaaaaaaaa catactccct cacaactctc                                    30

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
catactccct cacaactctc caactc                                        26

<210> SEQ ID NO 22
<211> LENGTH: 26
<212> TYPE: DNA
<213> ORGANISM: Artificial Sequence
<220> FEATURE:
<223> OTHER INFORMATION: Synthetic

<400> SEQUENCE: 22
gttgaggtga gatggaagga tgttgg                                        26

<210> SEQ ID NO 23
<211> LENGTH: 30
<212> TYPE: DNA
<213> ORGANISM: Artificial Sequence
<220> FEATURE:
<223> OTHER INFORMATION: Sythetic

<400> SEQUENCE: 23
aaaaaaaaaa ccaacatcct tccatctcac                                    30

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
ccaacatcct tccatctcac ctcaac                                        26

<210> SEQ ID NO 25
<211> LENGTH: 26
<212> TYPE: DNA
<213> ORGANISM: Artificial Sequence
<220> FEATURE:
<223> OTHER INFORMATION: Synthetic

<400> SEQUENCE: 25
gtgtagggag ggttgtagta ggaatg                                        26

<210> SEQ ID NO 26
<211> LENGTH: 30
<212> TYPE: DNA
<213> ORGANISM: Artificial Sequence
<220> FEATURE:
<223> OTHER INFORMATION: Synthetic

<400> SEQUENCE: 26
aaaaaaaaaa cattcctact acaaccctcc						30

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
cattcctact acaaccctcc ctacac						26

<210> SEQ ID NO 28
<211> LENGTH: 26
<212> TYPE: DNA
<213> ORGANISM: Artificial Sequence
<220> FEATURE:
<223> OTHER INFORMATION: Synthetic

<400> SEQUENCE: 28
gatgtgggtg gtgtaatgag tgagag						26

<210> SEQ ID NO 29
<211> LENGTH: 30
<212> TYPE: DNA
<213> ORGANISM: Artificial Sequence
<220> FEATURE:
<223> OTHER INFORMATION: Synthetic

<400> SEQUENCE: 29
aaaaaaaaaa ctctcactca ttacaccacc					30

<210> SEQ ID NO 30
<211> LENGTH: 26
<212> TYPE: DNA
<213> ORGANISM: Artificial Sequence
<220> FEATURE:
<223> OTHER INFORMATION: Synthetic

<400> SEQUENCE: 30
ctctcactca ttacaccacc cacatc						26

<210> SEQ ID NO 31
<211> LENGTH: 26
<212> TYPE: DNA
<213> ORGANISM: Artificial Sequence
<220> FEATURE:
<223> OTHER INFORMATION: Synthetic

<400> SEQUENCE: 31
ggataggtgg agaaggttga ggttag						26

<210> SEQ ID NO 32
<211> LENGTH: 30
<212> TYPE: DNA
<213> ORGANISM: Artificial Sequence
<220> FEATURE:
<223> OTHER INFORMATION: Synthetic

<400> SEQUENCE: 32
aaaaaaaaaa ctaacctcaa ccttctccac					30

<210> SEQ ID NO 33

<211> LENGTH: 26
<212> TYPE: DNA
<213> ORGANISM: Artificial Sequence
<220> FEATURE:
<223> OTHER INFORMATION: Synthetic

<400> SEQUENCE: 33
ctaacctcaa ccttctccac ctatcc                                    26

<210> SEQ ID NO 34
<211> LENGTH: 26
<212> TYPE: DNA
<213> ORGANISM: Artificial Sequence
<220> FEATURE:
<223> OTHER INFORMATION: Synthetic

<400> SEQUENCE: 34
gtaagggtgt aggtgaatag gtggag                                    26

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
aaaaaaaaaa ctccacctat tcacctacac                                30

<210> SEQ ID NO 36
<211> LENGTH: 26
<212> TYPE: DNA
<213> ORGANISM: Artificial Sequence
<220> FEATURE:
<223> OTHER INFORMATION: Synthetic

<400> SEQUENCE: 36
ctccacctat tcacctacac ccttac                                    26

<210> SEQ ID NO 37
<211> LENGTH: 26
<212> TYPE: DNA
<213> ORGANISM: Artificial Sequence
<220> FEATURE:
<223> OTHER INFORMATION: Synthetic

<400> SEQUENCE: 37
gtgaaggagt gagtgaggtt aagtgg                                    26

<210> SEQ ID NO 38
<211> LENGTH: 30
<212> TYPE: DNA
<213> ORGANISM: Artificial Sequence
<220> FEATURE:
<223> OTHER INFORMATION: Synthetic

<400> SEQUENCE: 38
aaaaaaaaaa ccacttaacc tcactcactc                                30

<210> SEQ ID NO 39
<211> LENGTH: 26
<212> TYPE: DNA
<213> ORGANISM: Artificial Sequence
<220> FEATURE:
<223> OTHER INFORMATION: Sythetic

<400> SEQUENCE: 39

```
ccacttaacc tcactcactc cttcac                                        26

<210> SEQ ID NO 40
<211> LENGTH: 26
<212> TYPE: DNA
<213> ORGANISM: Artificial Sequence
<220> FEATURE:
<223> OTHER INFORMATION: Synthetic

<400> SEQUENCE: 40
gagatgggat aagtaggtgt gggtag                                        26

<210> SEQ ID NO 41
<211> LENGTH: 30
<212> TYPE: DNA
<213> ORGANISM: Artificial Sequence
<220> FEATURE:
<223> OTHER INFORMATION: Synthetic

<400> SEQUENCE: 41
aaaaaaaaaa ctacccacac ctacttatcc                                    30

<210> SEQ ID NO 42
<211> LENGTH: 26
<212> TYPE: DNA
<213> ORGANISM: Artificial Sequence
<220> FEATURE:
<223> OTHER INFORMATION: Synthetic

<400> SEQUENCE: 42
ctacccacac ctacttatcc catctc                                        26

<210> SEQ ID NO 43
<211> LENGTH: 26
<212> TYPE: DNA
<213> ORGANISM: Artificial Sequence
<220> FEATURE:
<223> OTHER INFORMATION: Synthetic

<400> SEQUENCE: 43
gaagtggtgg ttaggaagtg agagtg                                        26

<210> SEQ ID NO 44
<211> LENGTH: 30
<212> TYPE: DNA
<213> ORGANISM: Artificial Sequence
<220> FEATURE:
<223> OTHER INFORMATION: Synthetic

<400> SEQUENCE: 44
aaaaaaaaaa cactctcact tcctaaccac                                    30

<210> SEQ ID NO 45
<211> LENGTH: 26
<212> TYPE: DNA
<213> ORGANISM: Artificial Sequence
<220> FEATURE:
<223> OTHER INFORMATION: Synthetic

<400> SEQUENCE: 45
cactctcact tcctaaccac cacttc                                        26

<210> SEQ ID NO 46
<211> LENGTH: 26
<212> TYPE: DNA
```

```
<213> ORGANISM: Artificial Sequence
<220> FEATURE:
<223> OTHER INFORMATION: Synthetic

<400> SEQUENCE: 46
gtagtggtga aatggtatgg gtggag                                            26

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
aaaaaaaaaa ctccacccat accatttcac                                        30

<210> SEQ ID NO 48
<211> LENGTH: 26
<212> TYPE: DNA
<213> ORGANISM: Artificial Sequence
<220> FEATURE:
<223> OTHER INFORMATION: Synthetic

<400> SEQUENCE: 48
ctccacccat accatttcac cactac                                            26

<210> SEQ ID NO 49
<211> LENGTH: 26
<212> TYPE: DNA
<213> ORGANISM: Artificial Sequence
<220> FEATURE:
<223> OTHER INFORMATION: Synthetic

<400> SEQUENCE: 49
gtatgggtgt ggtgtagaat ggagag                                            26

<210> SEQ ID NO 50
<211> LENGTH: 30
<212> TYPE: DNA
<213> ORGANISM: Artificial Sequence
<220> FEATURE:
<223> OTHER INFORMATION: Synthetic

<400> SEQUENCE: 50
aaaaaaaaaa ctctccattc tacaccacac                                        30

<210> SEQ ID NO 51
<211> LENGTH: 26
<212> TYPE: DNA
<213> ORGANISM: Artificial Sequence
<220> FEATURE:
<223> OTHER INFORMATION: Synthetic

<400> SEQUENCE: 51
ctctccattc tacaccacac ccatac                                            26

<210> SEQ ID NO 52
<211> LENGTH: 26
<212> TYPE: DNA
<213> ORGANISM: Artificial Sequence
<220> FEATURE:
<223> OTHER INFORMATION: Synthetic

<400> SEQUENCE: 52
ggtaaggtga gaggagtagg tatgtg                                            26
```

```
<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
aaaaaaaaaa cacataccta ctcctctcac                                      30

<210> SEQ ID NO 54
<211> LENGTH: 26
<212> TYPE: DNA
<213> ORGANISM: Artificial Sequence
<220> FEATURE:
<223> OTHER INFORMATION: Synthetic

<400> SEQUENCE: 54
cacataccta ctcctctcac cttacc                                          26

<210> SEQ ID NO 55
<211> LENGTH: 26
<212> TYPE: DNA
<213> ORGANISM: Artificial Sequence
<220> FEATURE:
<223> OTHER INFORMATION: Synthetic

<400> SEQUENCE: 55
gagtaggtgt gggaagtagg tgtaag                                          26

<210> SEQ ID NO 56
<211> LENGTH: 30
<212> TYPE: DNA
<213> ORGANISM: Artificial Sequence
<220> FEATURE:
<223> OTHER INFORMATION: Synthetic

<400> SEQUENCE: 56
aaaaaaaaaa cttacaccta cttcccacac                                      30

<210> SEQ ID NO 57
<211> LENGTH: 26
<212> TYPE: DNA
<213> ORGANISM: Artificial Sequence
<220> FEATURE:
<223> OTHER INFORMATION: Synthetic

<400> SEQUENCE: 57
cttacaccta cttcccacac ctactc                                          26

<210> SEQ ID NO 58
<211> LENGTH: 26
<212> TYPE: DNA
<213> ORGANISM: Artificial Sequence
<220> FEATURE:
<223> OTHER INFORMATION: Synthetic

<400> SEQUENCE: 58
gtgatgggta gggttgattg ggaaag                                          26

<210> SEQ ID NO 59
<211> LENGTH: 30
<212> TYPE: DNA
<213> ORGANISM: Artificial Sequence
<220> FEATURE:
```

<223> OTHER INFORMATION: Synthetic

<400> SEQUENCE: 59
aaaaaaaaaa ctttcccaat caaccctacc                                             30

<210> SEQ ID NO 60
<211> LENGTH: 26
<212> TYPE: DNA
<213> ORGANISM: Artificial Sequence
<220> FEATURE:
<223> OTHER INFORMATION: Synthetic

<400> SEQUENCE: 60
ctttcccaat caaccctacc catcac                                                 26

<210> SEQ ID NO 61
<211> LENGTH: 26
<212> TYPE: DNA
<213> ORGANISM: Artificial Sequence
<220> FEATURE:
<223> OTHER INFORMATION: Synthetic

<400> SEQUENCE: 61
gtagagggag agtattgtag aggtgg                                                 26

<210> SEQ ID NO 62
<211> LENGTH: 30
<212> TYPE: DNA
<213> ORGANISM: Artificial Sequence
<220> FEATURE:
<223> OTHER INFORMATION: Synthetic

<400> SEQUENCE: 62
aaaaaaaaaa ccacctctac aatactctcc                                             30

<210> SEQ ID NO 63
<211> LENGTH: 26
<212> TYPE: DNA
<213> ORGANISM: Artificial Sequence
<220> FEATURE:
<223> OTHER INFORMATION: Synthetic

<400> SEQUENCE: 63
ccacctctac aatactctcc ctctac                                                 26

<210> SEQ ID NO 64
<211> LENGTH: 26
<212> TYPE: DNA
<213> ORGANISM: Artificial Sequence
<220> FEATURE:
<223> OTHER INFORMATION: Synthetic

<400> SEQUENCE: 64
gatagggtaa gaatgggagt tggtgg                                                 26

<210> SEQ ID NO 65
<211> LENGTH: 30
<212> TYPE: DNA
<213> ORGANISM: Artificial Sequence
<220> FEATURE:
<223> OTHER INFORMATION: Synthetic

<400> SEQUENCE: 65
aaaaaaaaaa ccaccaactc ccattcttac                                             30

```
<210> SEQ ID NO 66
<211> LENGTH: 26
<212> TYPE: DNA
<213> ORGANISM: Artificial Sequence
<220> FEATURE:
<223> OTHER INFORMATION: Synthetic

<400> SEQUENCE: 66
ccaccaactc ccattcttac cctatc                                          26

<210> SEQ ID NO 67
<211> LENGTH: 26
<212> TYPE: DNA
<213> ORGANISM: Artificial Sequence
<220> FEATURE:
<223> OTHER INFORMATION: Synthetic

<400> SEQUENCE: 67
gattgggatg gtagggagtg tagatg                                          26

<210> SEQ ID NO 68
<211> LENGTH: 30
<212> TYPE: DNA
<213> ORGANISM: Artificial Sequence
<220> FEATURE:
<223> OTHER INFORMATION: Synthetic

<400> SEQUENCE: 68
aaaaaaaaaa catctacact ccctaccatc                                      30

<210> SEQ ID NO 69
<211> LENGTH: 26
<212> TYPE: DNA
<213> ORGANISM: Artificial Sequence
<220> FEATURE:
<223> OTHER INFORMATION: Synthetic

<400> SEQUENCE: 69
catctacact ccctaccatc ccaatc                                          26

<210> SEQ ID NO 70
<211> LENGTH: 26
<212> TYPE: DNA
<213> ORGANISM: Artificial Sequence
<220> FEATURE:
<223> OTHER INFORMATION: Synthetic

<400> SEQUENCE: 70
ggtatggtgg agagtgtgaa aggttg                                          26

<210> SEQ ID NO 71
<211> LENGTH: 30
<212> TYPE: DNA
<213> ORGANISM: Artificial Sequence
<220> FEATURE:
<223> OTHER INFORMATION: Synthetic

<400> SEQUENCE: 71
aaaaaaaaaa caacctttca cactctccac                                      30

<210> SEQ ID NO 72
<211> LENGTH: 26
<212> TYPE: DNA
<213> ORGANISM: Artificial Sequence
<220> FEATURE:
<223> OTHER INFORMATION: Synthetic
```

```
<400> SEQUENCE: 72
caacctttca cactctccac catacc                                          26

<210> SEQ ID NO 73
<211> LENGTH: 26
<212> TYPE: DNA
<213> ORGANISM: Artificial Sequence
<220> FEATURE:
<223> OTHER INFORMATION: Synthetic

<400> SEQUENCE: 73
gatgaggatg gatgaggtga ttgagg                                          26

<210> SEQ ID NO 74
<211> LENGTH: 30
<212> TYPE: DNA
<213> ORGANISM: Artificial Sequence
<220> FEATURE:
<223> OTHER INFORMATION: Synthetic

<400> SEQUENCE: 74
aaaaaaaaaa cctcaatcac ctcatccatc                                      30

<210> SEQ ID NO 75
<211> LENGTH: 26
<212> TYPE: DNA
<213> ORGANISM: Artificial Sequence
<220> FEATURE:
<223> OTHER INFORMATION: Synthetic

<400> SEQUENCE: 75
cctcaatcac ctcatccatc ctcatc                                          26

<210> SEQ ID NO 76
<211> LENGTH: 26
<212> TYPE: DNA
<213> ORGANISM: Artificial Sequence
<220> FEATURE:
<223> OTHER INFORMATION: Synthetic

<400> SEQUENCE: 76
ggaatggttg ggtgagagta gaagtg                                          26

<210> SEQ ID NO 77
<211> LENGTH: 30
<212> TYPE: DNA
<213> ORGANISM: Artificial Sequence
<220> FEATURE:
<223> OTHER INFORMATION: Synthetic

<400> SEQUENCE: 77
aaaaaaaaaa cacttctact ctcacccaac                                      30

<210> SEQ ID NO 78
<211> LENGTH: 26
<212> TYPE: DNA
<213> ORGANISM: Artificial Sequence
<220> FEATURE:
<223> OTHER INFORMATION: Synthetic

<400> SEQUENCE: 78
cacttctact ctcacccaac cattcc                                          26

<210> SEQ ID NO 79
<211> LENGTH: 26
```

```
<212> TYPE: DNA
<213> ORGANISM: Artificial Sequence
<220> FEATURE:
<223> OTHER INFORMATION: Synthetic

<400> SEQUENCE: 79
ggttagggtt tagatgagtg ggaagg                                           26

<210> SEQ ID NO 80
<211> LENGTH: 30
<212> TYPE: DNA
<213> ORGANISM: Artificial Sequence
<220> FEATURE:
<223> OTHER INFORMATION: Synthetic

<400> SEQUENCE: 80
aaaaaaaaaa ccttcccact catctaaacc                                       30

<210> SEQ ID NO 81
<211> LENGTH: 26
<212> TYPE: DNA
<213> ORGANISM: Artificial Sequence
<220> FEATURE:
<223> OTHER INFORMATION: Synthetic

<400> SEQUENCE: 81
ccttcccact catctaaacc ctaacc                                           26

<210> SEQ ID NO 82
<211> LENGTH: 26
<212> TYPE: DNA
<213> ORGANISM: Artificial Sequence
<220> FEATURE:
<223> OTHER INFORMATION: Synthetic

<400> SEQUENCE: 82
gaatgggata agttgggagt gggtag                                           26

<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83
aaaaaaaaaa ctacccactc ccaacttatc                                       30

<210> SEQ ID NO 84
<211> LENGTH: 26
<212> TYPE: DNA
<213> ORGANISM: Artificial Sequence
<220> FEATURE:
<223> OTHER INFORMATION: Synthetic

<400> SEQUENCE: 84
ctacccactc ccaacttatc ccattc                                           26

<210> SEQ ID NO 85
<211> LENGTH: 26
<212> TYPE: DNA
<213> ORGANISM: Artificial Sequence
<220> FEATURE:
<223> OTHER INFORMATION: Synthetic

<400> SEQUENCE: 85
```

```
ggattgggat agtgaaatgg tgtggg                                          26

<210> SEQ ID NO 86
<211> LENGTH: 30
<212> TYPE: DNA
<213> ORGANISM: Artificial Sequence
<220> FEATURE:
<223> OTHER INFORMATION: Synthetic

<400> SEQUENCE: 86
aaaaaaaaaa cccacaccat ttcactatcc                                      30

<210> SEQ ID NO 87
<211> LENGTH: 26
<212> TYPE: DNA
<213> ORGANISM: Artificial Sequence
<220> FEATURE:
<223> OTHER INFORMATION: Synthetic

<400> SEQUENCE: 87
cccacaccat ttcactatcc caatcc                                          26

<210> SEQ ID NO 88
<211> LENGTH: 26
<212> TYPE: DNA
<213> ORGANISM: Artificial Sequence
<220> FEATURE:
<223> OTHER INFORMATION: Synthetic

<400> SEQUENCE: 88
gttagggatg gaatggttag gaggtg                                          26

<210> SEQ ID NO 89
<211> LENGTH: 30
<212> TYPE: DNA
<213> ORGANISM: Artificial Sequence
<220> FEATURE:
<223> OTHER INFORMATION: Synthetic

<400> SEQUENCE: 89
aaaaaaaaaa cacctcctaa ccattccatc                                      30

<210> SEQ ID NO 90
<211> LENGTH: 26
<212> TYPE: DNA
<213> ORGANISM: Artificial Sequence
<220> FEATURE:
<223> OTHER INFORMATION: Synthetic

<400> SEQUENCE: 90
cacctcctaa ccattccatc cctaac                                          26
```

METHODS FOR MULTIPLEXED CELL ISOLATION USING DNA GATES

CROSS REFERENCE TO RELATED APPLICATIONS

This application is a national stage application, filed under 35 U.S.C. § 371, of International Patent Application No. PCT/US2019/017066 filed on Feb. 7, 2019, which claims benefit of and priority to U.S. Provisional Patent Application No 62/627,441 filed on Feb. 7, 2018, which are incorporated herein by reference in their entirety.

STATEMENT REGARDING FEDERALLY SPONSORED RESEARCH

This invention was made with government support under DP2HD091793 awarded by the National Institutes of Health. The government has certain rights in the invention.

REFERENCE TO A SEQUENCE LISTING

The Sequence Listing submitted Feb. 7, 2019 as a text file named 064489_039PCT_seglisting_ST25.txt" created on Feb. 7, 2019, and having a size of 16,675 bytes is hereby incorporated by reference pursuant to 37 C.F.R. § 1.52(e)(5).

TECHNICAL FIELD OF THE INVENTION

This invention is generally directed to multiplexed cell sorting systems and methods of their use.

BACKGROUND OF THE INVENTION

Biological specimens such as whole blood contain many different types of cells, and advances in cytometry and cell sorting technologies have led to fundamental insights in cell biology and important applications in biomedicine (Bendall, S C., et al., *Trends Immunol*, 33:323-332 (2012); Jaye, D L., et al., *J Immunol*, 188:4715-4719 (2012); Spitzer, M H., et al., *Cell*, 165:780-791 (2016)). For example, in fluorescent-based platforms such as fluorescence-activated cell sorting (FACS), each different cell type is labeled with fluorophore-tagged antibodies and sorted along fluorescent gates. This well-established approach has been used to define new types of stem cells (Kondo, M., et al., *Cell*, 91:661-672 (1997); Morikawa, S., et al., *J Exp Med*, 206:2483-2496 (2009); Tani, et al., *Proc Natl Acad Sci USA*, 97:10960-10965 (2000); Uchida, N., et al., *Proc Natl Acad Sci USA*, 97:14720-14725 (2000)), discover biomarkers for cancer (Wang, W., et al., *J Transl Med*, 10:146 (2016); Daud, Al et al., *J Clin Invest*, 126:3981-3991 (2015)), and isolate rare cells for cell-based therapies (Cohen, C J., et al., *J Clin Invest*, 125:3981-3991 (2015); De Coppi, P., et al., *Nat Biotechnol*, 25:100-106 (2007)). However, for complex systems involving many different types of cells, sorting by fluorescence-activated cell sorting is challenging because only a limited number of fluorophores can be used simultaneously due to overlapping emission spectra. This has led to the development of methods such as combinatorial staining (Newell, E W., et al., *Nat Methods*, 6:497-499 (2009); Hadrup, S R., et al., *Nat Methods*, 6:520-526 (2009)) and fluorescent cell barcoding (FCB) (Krutzik, P O, et al., *Nat Methods*, 3:361-368 (2006)) to improve the multiplexing capacity of flow cytometry, enabling applications such as high-content single-cell drug screening (Krutzik, P O., et al., *Nat Chem Biol*, 4:132-142 (2008)).

The emergence of cytometry by time of flight (CyTOF) takes an entirely different approach by staining surface markers with heavy metal tags in lieu of fluorophores and then analyzing cells by mass spectrometry. Because the number of unique heavy metals exceeds the number of spectrally distinct fluorophores that can be combined in a single staining panel, CyTOF allows analysis of systems that would otherwise be challenging by flow, such as mapping cellular differentiation pathways (e.g., hematopoiesis) (Bendall, S. C., et al., *Science*, 332:687-696 (2011); Qiu, P., et al., *Nat Biotechnol*, 29:886-891 (2011); Porpiglia, E., et al., *Nat Cell Biol*, 19:558-567 (2017)) and analyzing single cells at a systems level (Bodenmiller, B., et al., *Nat Biotechnol*, 30:858-867 (2012); Newell, E W., et al., *Immunity*, 36:142-152 (2012); Spitzer, M H., et al., *Cell*, 168:487-502)). However, in CyTOF, cells are ionized during detection, limiting throughput and preventing recovery of cells for downstream functional assays. In addition, current cell sorting technologies require expensive and large pieces of equipment and can only isolate a few types of cells at one time.

Thus, there is a need for improved systems and methods for sorting cells.

It is an object of the invention to provide systems and methods for high-throughput cell sorting.

SUMMARY OF THE INVENTION

Systems and methods for multiplex cell sorting are provided. One embodiment provides systems and methods for orthogonal DNA-gated sorting for performing multiplexed cell sorting. In another embodiment, the systems and methods perform multiplexed cell sorting on a scale that exceeds the use of cell sorting systems that use fluorophore tags. For example, in some embodiments a heterogeneous cell population can be sorted using at least 20, 50, 100, 1,000, or 10,000, 100,000, or 1,000,000 unique nucleic acid probes to separate the heterogeneous population into multiple isolated cell populations of different phenotypes. In one embodiment, the disclosed cell sorting system is a high-through put system. The high-through put cell sorting system can be partially or completely automated.

Another embodiment provides a probe for cell sorting including a single-stranded nucleic acid targeting probe conjugated to a binding moiety via a single-stranded toehold domain, wherein the nucleic acid targeting probe includes a complementary single-stranded nucleic acid catch probe annealed to the nucleic acid targeting probe, and wherein the nucleic acid catch probe includes a magnetic bead. In some embodiments the 5' end of the toehold domain is linked or conjugated to the binding moiety. The toehold can have 3 to 10 nucleotides and the single-stranded targeting probe can have 3 to 30 nucleotides. The binding moiety of the sorting probe can be an antibody or antigen binding fragment thereof, a fusion protein, an aptamer, peptide-MHC, multivalent construct containing peptide MHC, a ligand for a cell surface receptor, or cell surface protein. In some embodiments the binding moiety specifically binds to a cell surface protein, cell surface glycoprotein, cell surface polysaccharide, or a cell surface lectin. In one embodiment, the magnetic bead is conjugated to the catch probe by a biotin-streptavidin interaction. In some embodiments, the toehold is conjugated to an Fc region.

Another embodiment provides a cell including one of the disclosed probes bound to the cell's surface.

Also provided is a method of sorting cells including steps of a) labeling a heterogeneous population of cells with at least one of the disclosed probes for cell sorting, wherein the binding moiety of the at least one probe for cell sorting specifically binds to a cell surface protein or cell surface receptor expressed by one type of cells in the heterogeneous population; b) subjecting the heterogeneous cell population of step a) to magnetic cell sorting to separate cells expressing the cell surface protein or cell surface receptor bound by the probe from cells that are not bound by the probe, c) contacting the separated cells bound by the at least one probe for cell sorting with at least one single-stranded nucleic acid release probe having a complementary sequence to the targeting probe of the at least one probe for cell sorting, wherein the catch probe is released from the at least one probe for cell sorting when the release probe anneals to the targeting probe, and collecting the separated cells.

One embodiment provides a multiplex method of sorting cells, including the steps of a) labeling a heterogeneous population of cells with at least a first probe for cell sorting and a second probe for cell sorting, wherein the binding moiety of the first probe for cell sorting specifically binds to a first cell surface protein or a first cell surface receptor expressed by one type of cells in the heterogeneous population and the binding moiety of the second probe for cell sorting specifically binds to a second and different cell surface protein or a second and different cell surface receptor expressed by one type of cells in the heterogeneous population and optionally, a different targeting probe sequence than that of the first probe for cell sorting; b) subjecting the heterogeneous cell population of step a) to magnetic cell sorting to separate cells expressing the cell surface protein or cell surface receptor bound by the first and second probes for cell sorting, c) contacting the separated cells of step b) with a first single-stranded nucleic acid release probe having a complementary sequence to the targeting probe of the first probe for cell sorting, wherein the catch probe is released from the first probe for cell sorting when the release probe anneals to the toehold, and d) collecting the separated cells from step c); e) contacting the separated cells from step b) with a second single-stranded nucleic acid release probe having a complementary sequence to the targeting probe of the second probe for cell sorting, wherein the catch probe is released from the second probe for cell sorting when the release probe anneals to the targeting probe; and f) collecting the separated cells from step e).

Another embodiment provides a multiplex method of sorting cells, including the steps of a) labeling a heterogeneous population of cells with a plurality of probes for cell sorting, wherein each of the plurality of the probes comprises a different binding moiety and optionally a different toehold sequence for the other probes for cell sorting; b) subjecting the heterogeneous cell population of step a) to magnetic cell sorting to separate cells bound by one or more of the plurality of probes for cell sorting; c) contacting the separated cells of step b) with a first single-stranded nucleic acid release probe having a complementary sequence to the targeting probe of a first probe of the plurality of probes for cell sorting, wherein the catch probe is released from the first probe of the plurality of probes for cell sorting when the first release probe anneals to the targeting probe, d) collecting the separated cells from step c); and e) sequentially repeating steps c)-d) with a single stranded nucleic acid release probe specific for each of the remaining plurality of probes to sequentially separate and collect cells bound by each of the remaining plurality of probes for cell sorting.

Also provided is a method of isolating cancer cells, including the steps of a) labeling a heterogeneous population of cells with at least one probe for cell sorting, wherein the binding moiety of the at least one probe for cell sorting specifically binds to a cancer cell surface protein or cancer cell surface receptor expressed by one type of cells in the heterogeneous population; b) subjecting the heterogeneous cell population of step a) to magnetic cell sorting to separate cells expressing the cancer cell surface protein or cancer cell surface receptor bound by the binding moiety from cells that are not bound by the binding moiety, c) contacting the separated cells bound by the at least one probe for cell sorting with at least one single-stranded nucleic acid release probe having a complementary sequence to the targeting probe of the at least one probe for cell sorting, wherein the catch probe is released from the at least one probe for cell sorting when the release probe anneals to the targeting probe, and d) collecting the separated cells from step c).

Another embodiment provides a method of isolating cancer stem cells, including the steps of a) labeling a heterogeneous population of cells with at least one probe for cell sorting, wherein the binding moiety of the at least one probe for cell sorting specifically binds to a cancer stem cell surface protein or cancer stem cell surface receptor expressed by one type of cells in the heterogeneous population; b) subjecting the heterogeneous cell population of step a) to magnetic cell sorting to separate cells expressing the cell surface protein or cell surface receptor bound by the binding moiety from cells that are not bound by the binding moiety, c) contacting the separated cells bound by the at least one probe for cell sorting with at least one single-stranded nucleic acid release probe having a complementary sequence to the targeting probe of the at least one probe for cell sorting, wherein the catch probe is released from the at least one probe for cell sorting when the release probe anneals to the targeting probe, and d) collecting the separated cells from step c).

Another embodiment provides a method of isolating antigen-specific cells, including the steps of a) labeling a heterogeneous population of cells with at least one probe for cell sorting, wherein the binding moiety of the at least one probe for cell sorting specifically binds to an antigen receptor expressed by one type of cells in the heterogeneous population; b) subjecting the heterogeneous cell population of step a) to magnetic cell sorting to separate cells expressing the antigen receptor bound by the binding moiety from cells that are not bound by the binding moiety, c) contacting the separated cells bound by the at least one probe for cell sorting with at least one single-stranded nucleic acid release probe having a complementary sequence to the targeting probe of the at least one probe for cell sorting, wherein the catch probe is released from the at least one probe for cell sorting when the release probe anneals to the targeting probe, and d) collecting the separated cells from step c).

The heterogeneous population of cells that can be sorted using the disclosed methods can include cells from a biological specimen selected from the group consisting of a biopsy, tissue, blood, serum, plasma, lymphatic fluid, biological fluid, or a tumor. The sorted cells can be immune cells, epithelial cells, neuronal cells, muscle cells, fibroblasts, diseased cells, cancer cells, infected cells, or cells genetically engineered to express a cell surface protein or cell surface receptor that binds the at least one probe for cell sorting.

One embodiment provides a method of sorting a heterogeneous population of cells into subsets of cells having unique cell surface molecule expression patterns. In this embodiment, a heterogeneous population of cells, for example immune cells, is contacted with one or more of the disclosed probes for cell sorting. Each probe is designed to bind to a different cell surface molecule, including but not limited to cell surface proteins, cell surface receptors, ligand for cell surface receptors, lectins, polysaccharides, and combinations thereof. Once the probes are allowed to bind to the cell surface molecules that may be present on the cells in the heterogeneous population, the labeled cells are magnetically sorted into a first subset of cells that express a subset of the cell surface molecules bound by the one or more probes and a second subset of cells that do not express the cell surface molecules and are not bound by the probes. The cells that are not bound by the probes do not express the cell surface molecule recognized by the probe. In this embodiment, the second subset of cells is then contacted with N number of probes wherein each of the N number of probes specifically binds to a unique cell surface molecule. The cells labeled with the N number of probes are then magnetically sorted to isolate cells having a desired expression pattern of cell surface markers by contacting the cells from step with one or more release probes that specifically anneal to the N number of probes that bind the cell surface molecules of the desired expression pattern. The released cells are isolated from the cells bound by the probes having magnetic beads. The isolated cells contacted with the N number of probes do not express the cell surface molecule bound by the one or more probes and do express the desired expression pattern of cell surface markers bound by the N number of probes.

One embodiment provides a method of isolating antigen presenting cells. In this embodiment, a heterogeneous population of cells including antigen-presenting cells us contacted with one or more of the disclosed probes for sorting. The binding moiety of the probes includes a T cell receptor complex displaying a peptide antigen. Once the cells are contacted with the probes, cells bounds by the probes are magnetically separated into a sub population of cells, wherein the cells bound by the one or more probes are antigen presenting cells, such as dendritic cells, macrophages, or B lymphocytes.

Also provided is a method of promoting an antigen specific immune response in a subject in need. This method includes isolating immune cells from the subject, sorting the isolated immune cells according to the disclosed cell sorting methods, and administering the isolated cells to the subject to promote an antigen specific immune response in the subject, such as an anti-cancer response, an anti-viral response, or an anti-bacterial response. The sorting can occur ex vivo. The immune response can be the activation of killer T cells Another embodiment provides a kit for cell sorting including one or more probes for cell sorting, and one or more release probes, wherein the release probes include a single-stranded nucleic acid probe having a complementary sequence to the targeting probe of the one or more probes for cell sorting. The binding moiety of the cell sorting probe can be an antibody or antigen binding fragment thereof, a peptide-MHC, a fusion protein, an aptamer, or a ligand for a cell surface receptor or cell surface protein. The binding moiety of the cell sorting probe specifically binds to a cell surface protein, a cell surface receptor, or a cell surface molecule such as a polysaccharide. The kit can additionally include buffers for magnetic sorting cells from a heterogeneous cell population.

BRIEF DESCRIPTION OF THE DRAWINGS

FIG. 1A-FIG. 1C are schematic illustrations of multiplexed cell sorting by orthogonal antibody DNA gates. FIG. 1A shows Step 1 wherein antibodies encoded with a targeting probe bind to cell surface markers on target cells. FIG. 1B shows Step 2 wherein the release probes displace the catch probe through toehold-mediated strand displacement, removing the magnetic label from target cells. FIG. 1C shows Step 3 wherein target cells are recovered due to the absence of the magnetic label. FIGS. 1D-1E are illustrations showing the workflow of FACS sorting of labeled cells (FIG. 1D) and DNA gate sorting of labeled cells (FIG. 1E).

FIGS. 4I-4K are flow plots showing frequency of CD8+ cells in the native tissue (FIG. 4I), unlabeled fractions after DGS (FIG. 4J), and labeled fractions after DGS (FIG. 4K). FIGS. 4L-4N are bar graphs showing comparison of CD8+ cell sorting purity (FIG. 4L), viability (FIG. 4M), and yield (FIG. 4N) yield by DGS and MACS.

FIGS. 5A-5C are flow plots assessing CD8+ purity after DGS sorting and FIGS. 5D-5F are flow plots assessing CD8+ purity after MACS sorting. FIGS. 5G-5I are flow plots assessing CD8+ viability after DGS sorting and FIGS. 5J-5L are flow plots assessing CD8+ viability after MACS sorting.

FIGS. 6B-6D are graphs showing cell frequencies of B220+ (FIG. 6B), CD8+ (FIG. 6C), and CD4+ (FIG. 6D) in splenocytes from C57BL/6J mice. FIGS. 6E-6G are graphs showing the frequency of CD19-labeled B220+(FIG. 6E), CD8+ (FIG. 6F), and CD4+ (FIG. 6G) splenocytes. FIGS. 6P-6Q are flow plots showing the production of granzyme B in CD8+ cells purified by DGS and co-incubated with EL4 (FIG. 6P) or EG7-OVA (FIG. 6Q).

FIG. 9A is a schematic showing dual-gated DGS antibodies and pMHC tetramers. Quenched DNA gates are site-specifically conjugated to pMHC tetramers. Upon addition of the corresponding RP, the quencher-labeled CP is displaced by strand displacement. FIGS. 9B-9C are plots showing fluorescence signal from splenocytes from P14 (FIG. 9B) and pmel (FIG. 9C) TCR transgenic mice stained with corresponding quenched tetramer-TP$^B$:CP$^B$ complexes after addition of RP$^B$ strands. FIG. 9D is a schematic showing the sorting strategy used for FIGS. 9E-9J. FIGS. 9E-9G show the frequency of CD8+ (FIG. 9E), p14+ (FIG. 9F) and pmel+ (FIG. 9G) splenocytes before sorting. FIGS. 9L-9O show the frequencies of GP276-specific T cells in the spleen (FIG. 9L) and after sorting by DGS (FIGS. 9M-9N). FIGS. 9P-9S show the frequencies of NP205-specific T cells in the spleen (FIG. 9P) and after sorting by DGS (FIGS. 9Q-9R). Specificity of isolated cells was verified by staining with allele matched control tetramer. Data shown is gated on CD8+ cells.

FIGS. 11A-11D are plots that show the frequency of CD4+ T cells and B220+B cells in splenocytes from LCMV infected mice before sorting (FIGS. 11A and 11B, respectively) and after sorting from by DGS (FIGS. 11C and 11D, respectively). FIGS. 11E-11H are flow plots showing the frequency of LCMV-specific T cell populations before (FIGS. 11E-11F) and after (FIGS. 11G-11H) sorting by DGS.

DETAILED DESCRIPTION OF THE INVENTION

I. Definitions

Figures 2A, 2B, 2C:
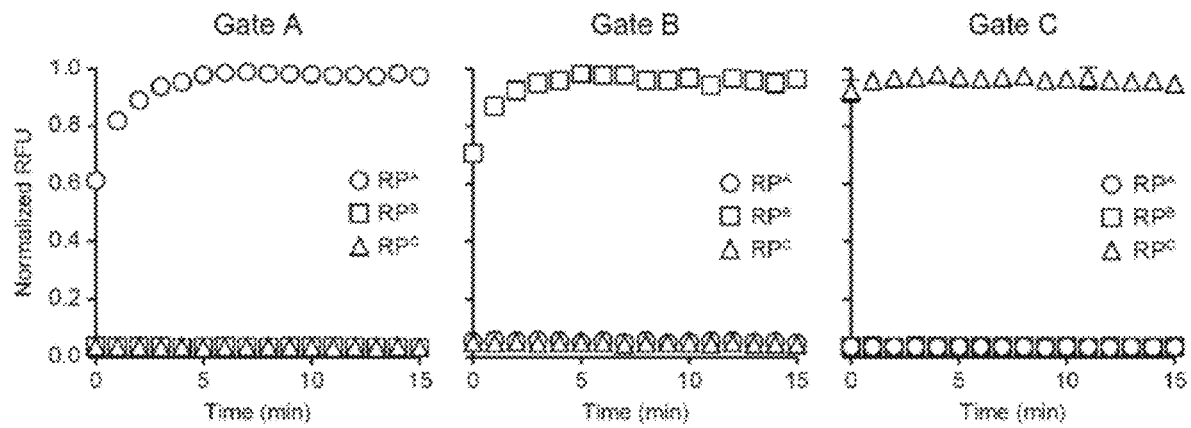
FIGS. 2A-2C are scatter plots showing the kinetics of free DNA gates in solution for $RP^A$ (○) $RP^B$ (□), and $RP^C$ (Δ) for Gate A (FIG. 2A), Gate B (FIG. 2B), and Gate C (FIG. 2C).

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm.* Biotech. 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, "gating" refers to the process of selecting the population of cells to be sorted or analyzed. In FACS sorting, this process involves selecting an area on the scatter plot generated during the flow experiment, typically using forward scatter and side scatter to find viable single cell events.

As used herein, "complementary nucleic acid" or "complementary DNA" refers to a strand of DNA or RNA that will pair with, or complement, a second strand of DNA or RNA.

As used herein, "orthogonal DNA gates" or "orthogonal interaction" refers to the interaction between two pairs of substances in which each substance can only interact with their respective partner, but does not interact with either substance of another pair of substances. For example, DNA gate A interacts with release probe 1 and DNA gate B interacts with release probe 2 but DNA gate A cannot interact with release probe 2 and DNA gate B cannot interact with release probe 1.

"Toehold-mediated strand displacement" refers to a mechanism in which nucleic acid complexes are reconfigured in response to the addition of a new nucleic acid strand. In this type of reaction, the new, or incoming, strand of nucleic acid binds to a single-stranded region of a double-stranded complex, called a toehold domain. The new strand displaces one of the strands bound in the original complex through branch migration. The result is that one of the strands in the original complex is replaced with another strand.

As used herein, "nucleic acid hybridization" or "DNA hybridization" refer to a phenomenon in which single-stranded nucleic acid molecules anneal to a complementary nucleic acid. "Hybridization domain" as used herein, refers to the portion of a strand of a nucleic acid that will anneal to a complementary nucleic acid.

As used herein, the terms "affinity agent" and "cell capture agent" refer to substances that can recognize and bind to cells in a biological sample. Exemplary affinity agents and cell capture agents include but are not limited to antibodies, antigen-binding fragments, fusion proteins, aptamers, small molecules, and polypeptides.

As used herein, the terms "individual," "host," "subject," and "patient" are used interchangeably herein, and refer to a mammal, including, but not limited to, humans, rodents, such as mice and rats, and other laboratory animals.

As used herein, "heterogeneous population" and "heterogeneous cell population" refers to a population of cells having two or more different types of cells, identified by cell surface markers.

II. DNA Gated-Cell Sorting System

Systems and methods for sorting cells are provided. The ability to sort and analyze specific cell populations from a biological specimen is important in cell biology and biomedicine to help elucidate mechanisms of disease and to discover new therapies. One embodiment provides a system to capture, release, and recover target cells from a biological specimen. The system and methods are referred to as "DNA-gated sorting" (DGS). DNA gates, or nucleic acid gates, are nucleic acid probes that are made of different strand displacement reactions that can be uniquely mapped to cell surface markers through coupling to affinity agents (also referred to as binding moieties).

An exemplary system provides probes for sorting cells of one or more different cell types or one or more phenotypes from a biological specimen. In one embodiment the complete probe for sorting cells contains a single-stranded nucleic acid targeting probe. One end of the targeting probe is conjugated or linked to a binding moiety, including but not limited to an antibody or antigen binding fragment thereof, a fusion protein, an aptamer, a lectin, a cell surface receptor protein, and a cell surface receptor ligand. The complete probe also contains a single-stranded nucleic acid catch probe that contains a magnetic bead linked or conjugated to one end of the catch probe. The catch probe contains a nucleic acid sequence that is complementary to the nucleic acid sequence of the targeting probe. In the complete probe, the catch probe is annealed to targeting probe.

The nucleic acids of the complete probe can be DNA, RNA or a combination thereof. In some embodiments, the nucleic acids include non-naturally occurring nucleic acids. In still other embodiments the nucleic acids contain nucleotides that form cleavage resistant bonds including but not limited to phosphorothioate bonds.

The binding moiety of the complete probe targets the complete probe to a desired cell type, cell phenotype, or tissue type by specifically binding to a cell surface marker on a target cell. The cell surface marker is typically a biological marker that is expressed on the surface of the cell. Cell surface markers include, but are not limited to cell surface proteins, cell surface saccharides, cell surface lectins, cell surface protein receptors, cell surface ligands for receptors, viral proteins or fragments thereof, and T cell receptor complexes. Cell phenotypes can be used to separate developmentally mature cells from immature cells, infected cells from non-infected cells, and dysfunctional cells from healthy cells.

The magnetic bead of the catch probe allows cells bound by the complete probe to be sorted using a magnetic cell sorter. The catch probe can be released from the complete probe by contacting the complete probe with a single-stranded nucleic acid complementary to the targeting probe nucleic acid sequence (the release probe). Binding of the release probe to the toehold displaces the catch probe and thereby releases the magnetic bead from the complete probe bound to the target cell. The cells without the magnetic bead attached to the complete probe can be collected or isolated from the cells bound by probes containing the magnetic bead.

In some embodiments, a heterogeneous cell population is contacted with multiple probes each having a unique targeting probe sequence. A heterogeneous cell population labeled with multiple probes having unique targeting probe sequences enables the isolation of multiple types of cells from the heterogeneous cell population by sequentially or alternatively contacting the labeled heterogeneous cell population with specific release probes complementary to specific targeting probes targeted to the cell type to be isolated. Each different cell type to be isolated can be sequentially isolated by contacting the labeled heterogeneous cell population by sequentially contacting the labeled cell population with probe containing different toehold nucleic acid sequences. The heterogeneous cell population can be obtained from a biopsy, tissue, blood, serum plasma, lymphatic fluid, biological fluid, or a tumor.

A. Probes for Cell Sorting

As generally discussed above, the complete probe for cell sorting includes a toehold nucleic acid, a targeting probe nucleic acid, a catch probe nucleic acid, and a binding moiety conjugated or linked to the one end of the toehold nucleic acid. A release probe is used to release the catch probe and thereby facilitate the separation of desired cells.

1. Targeting Probe

In one embodiment, the complete probe for cell sorting includes a single-stranded nucleic acid targeting probe. The targeting probe can contain a single-stranded toehold domain and a hybridization domain. The nucleic acid sequence of the targeting probe can be DNA, RNA, ssDNA, ssRNA, locked nucleic acids, zip nucleic acids, xeno nucleic acids, nucleic acids using unnatural nucleobases, or other nucleic acid analogues or a combination thereof. In some embodiments, the nucleic acid targeting probe contains non-naturally occurring nucleotides. The nucleic acid targeting probe is designed to hybridize with and anneal to the catch probe. Thus, the nucleic acid sequence of the target probe or at least a portion of the nucleic acid sequence of the target probe is complementary to the nucleic acid sequence of the capture probe or to at least a portion of the nucleic acid sequence of the capture probe sufficient to anneal target probe to the capture probe. In one embodiment, all or part of the nucleic acid sequence of the targeting probe is complementary to all or part of the nucleic acid sequence of the capture probe of the sorting probe.

In one embodiment, the single-stranded toehold domain of the targeting probe does not anneal to the capture probe. The toehold domain of the targeting probe is conjugated or linked to a binding moiety. In some embodiments, the 5' end of the toehold domain is conjugated or linked to the binding moiety, and the 3' end of the toehold is conjugated or linked to the hybridization domain. The toehold domain serves to facilitate release of the capture probe when the release probe anneals to the nucleic acid sequence of the toehold and thereby displaces the capture probe. The rate of strand-displacement reactions can be controlled by varying the length and sequence (G-C content) of the toehold domain. In one embodiment, the toehold domain has about 3-10 nucleotides. In one embodiment, the toehold domain contains at least 6 bases. In another embodiment, the toehold domain has a G or a C on the 5' end. The toehold domain can have from about 30% to about 70% G-C content. In some embodiments toehold domain has at least 50% G-C content. In one embodiment, the full length targeting probe contains 3-30 nucleotides, preferably 10-30 nucleotides. The nucleic acid sequence of the full length targeting probe as at least 50% G-C content. In one embodiment, the full length targeting probe has about 30% to about 70% G-C contents.

2. Binding Moieties

The binding moiety conjugated or linked to the targeting probe binds to molecules expressed on or attached to the surface of a cell. The binding moiety can be an antibody or antigen binding fragment thereof, a fusion protein, an aptamer, pMHC, a lectin, a saccharide, a ligand for a cell surface receptor, or a receptor that binds to ligands on cell surfaces. The binding moiety can be conjugated to the cell sorting probe using methods known in the art. In one embodiment, the cell sorting probe is conjugated to the antibody through the introduction of a linker that forms a covalent conjugate between the cell sorting probe and the binding moiety. Exemplary reactions that can be used to link the binding moieties include but are not limited to amine-to-amine crosslinkers using NHS esters, thiol-to-thiol cross-linkers using maleimides, amine-to-thiol crosslinkers using NHS esters and maleimides, and biotin/streptavidin interactions.

The binding moiety can target molecules on the surface of human or mouse cells, or cells from laboratory animals such as rabbits, goats, rats, hamsters, guinea pigs, sheep, dogs, cats, monkeys, chimpanzees, and apes, or from established cell lines. In one embodiment, the binding moiety specifically binds to a cluster of differentiation (CD) molecule. Exemplary human CD markers that can be bound by the binding moiety include but are not limited to T cell markers, such as CD3, CD4, and CD8; B cell markers, such as CD19 and CD20; dendritic cell markers, such as CD11c and CD123; NK cell markers such as CD56; stem cell markers, such as CD34; macrophage/monocyte markers such as CD14 and CD33; granulocyte markers such as CD66b; platelet markers such as CD41, CD61, and CD62; erythrocyte markers such as CD235a; endothelial cell markers such as CD146; and epithelial cell markers such as CD326. Exemplary mouse CD markers include but are not limited to T cell markers, such as CD3, CD4, and CD8; B cell markers, such as CD45R/B220, CD19, and CD22; dendritic cell markers, such as CD11c and CD123; NK cell markers such as CD335; stem cell markers, such as CD34; macrophage/monocyte markers such as CDT1b/Mac-1 and Ly-71 (F4/80); granulocyte markers such as CD66b, Gr-1/Ly6G, and Ly6C; platelet markers such as CD41, CD61 (Integrin β3), CD9, and CD62P; erythrocyte markers such as CD235a and Ter-119; endothelial cell markers such as CD146 MECA-32, CD106, CD31, and CD62E; and epithelial cell markers such as CD326 (EPCAM1).

In one embodiment the binding moiety can specifically bind to cell surface proteins, antigens, or receptors expressed on cancer cells. Exemplary cell surface proteins, antigens, or receptors expressed on cancer cells that can be specifically bound by the binding moieties include but are not limited to human epidermal growth factor receptors (HER2), estrogen receptors, MUC1, prostate specific membrane antigen (PSMA), carcinoembryonic antigen (CEA), EphA2, EpCAM, androgen receptors, prostate stem cell antigen (PSCA), mesothelin, and HA17. In another embodiment the binding moieties target cancer stem cell markers such as but not limited to CD133, CD44, and CD166.

Other cell surface markers that can be specifically bound by the binding moieties include but are not limited to cell surface receptors or cell surface proteins such as T cell receptors, B cell receptors, tumor necrosis factor receptors, glycoproteins, MHCs, immunoglobulins, integrins, cadherins, EGFR, VEGFR, PD-1, PD-L1, CTL4, virus proteins, bacterial proteins, and mucins.

In another embodiment the binding moiety can bind a peptide MHC complex or a multivalent construct containing peptide MHC. MHC molecules bind peptide fragments derived from pathogens and display them on the cell surface for recognition by appropriate T cell receptors. The MHC gene family is divided into three subgroups: class I, class II, and class III. Class I MHC molecules have 2 subunits which can only be recognized by CD8 co-receptors. Class II MHC molecules have 1 and 2 subunits and can be recognized by CD4 co-receptors. In this way MHC molecules chaperone which type of lymphocytes may bind to the given antigen with high affinity, since different lymphocytes express different T cell receptors. MHC can display antigens derived from viruses, intracellular bacteria, or protozoan parasites, or exogenous pathogens that replicate outside of the cell. In one embodiment, the antigens displayed by MHC can be cancer antigens, viral antigens, or bacterial antigens. In one embodiment, the binding moiety targets peptide MHC complexes unique to different T cells.

3. Catch Probe

The single-stranded nucleic acid catch probe is designed to hybridize to and anneal to all or part of the nucleic acid targeting probe. The single-stranded nucleic acid catch probe can be DNA, RNA, ssDNA, ssRNA, locked nucleic acids, zip nucleic acids, xeno nucleic acids, nucleic acids using unnatural nucleobases, or other nucleic acid analogues or a combination thereof. In some embodiments, the nucleic acid catch probe contains non-naturally occurring nucleotides. In one embodiment, the entire length of the catch probe hybridizes with the all or part of the nucleic acid targeting probe. Thus, the nucleic acid targeting probe and the nucleic acid catch probe can be of different lengths. In one embodiment, the catch probe contains 3-30 nucleotides, preferably 10-30 nucleotides. The catch probe can have 80%, 85%, 90%, 91%, 92%, 93%, 94%, 95%, 96%, 97%, 98%, 99%, or 100% sequence identity to the all or part of the complementary nucleic acid sequence of the targeting probe. In one embodiment, the catch probe has at least 50% G-C content. The catch probe can have between about 30% to about 70% G-C.

In one embodiment, the catch probe is coupled to a molecule that facilitates sorting of cells bound by the complete probe. In one embodiment, the molecule is a magnetic bead. In another embodiment the probes can be attached to a fixed surface, polymer microspheres, nanoparticles, other cells, or polymer scaffolds. There are a variety of commercially available magnetic beads that can be conjugated to RNA, DNA, and protein. Exemplary magnetic beads include but are not limited to Dynabeads® Biotin Binder (Invitrogen™) Dynabeads™ M-280 Streptavidin, and MACS Microbeads (Miltenyi Biotec). In one embodiment, the catch probe is conjugated or linked to the magnetic bead by a biotin:streptavidin linkage.

In some embodiments, the catch probe includes additional elements such as a spacer region between the catch probe the magnetic bead. In one embodiment, the spacer region is a poly(A)$_{10}$ region.

In some embodiments, the targeting probe and catch probe are pre-hybridized to form complete sorting probes before addition of the probes to the biological specimen. In another embodiment, the targeting probe and the catch probe are not pre-hybridized before addition to the biological specimen. Upon addition of the sorting probes to the biological specimen, a complex will form between the target cells and the cell targeting sorting probes conjugated to a magnetic bead.

4. Release Probe

In one embodiment, each sorting probe has a corresponding nucleic acid release probe that specifically hybridizes to and anneals with the unique nucleic acid sequence of the toehold domain of the targeting probe. In one embodiment, the release probe has 80%, 85%, 90%, 91%, 92%, 93%, 94%, 95%, 96%, 97%, 98%, 99%, or 100% sequence identity to the nucleic acid toehold domain In some embodiments, the entire length of the release probe is complementary to the entire length of the toehold. In one embodiment, the release probe has 3-10 nucleotides. In one embodiment, the release probe has at least 50% G-C content. The release probe can have about 30% to about 70% G-C content.

B. Kits

One embodiment provides a kit for sorting cells. An exemplary kit contains one or more of the closed probes for cell sorting and optionally buffers, reagents, and written directions for using the kit to sort cells. In one embodiment the kit contains a complete probe as described above. The complete probe includes a toehold conjugated to a binding moiety and a targeting probe. The targeting probe is hybridized/annealed to a capture probe containing a magnetic bead. The kit also includes a release probe. The kit can contain custom designed probes and release probes to sort one more types of cells. In some embodiments, the capture probe is provided independently from the complete probe so that the capture probe is not annealed to the targeting probe.

In one embodiment, the disclosed kit can include buffers and solutions necessary to perform magnetic cell sorting. Exemplary buffers and solutions necessary for running magnetic cell sorting include but are not limited to washing buffer, running buffer, and rinsing solution.

Other buffers and solutions that can be included in the disclosed cell sorting kits include buffers useful for storing biological specimens, buffers used for cell culture and the production of single-cell suspensions, and buffers useful for storing and mixing the DNA-gates and release probes. Exemplary solutions and buffers could include but are not limited to phosphate buffered saline (PBS), Tris-EDTA buffer, HEPES, HBSS, PBS containing bovine serum antigen (BSA) and DNA suspension buffer.

III. Methods of Use

The disclosed DNA-gated sorting kits can be used to isolate cells based on the expression of specific cell surface markers or cell surface receptors. The orthogonal nature of the sorting probe/release probe pairs allows for a unique sorting probe to be assigned to each cell surface marker. Magnetic isolation can be performed en masse, meaning multiple sorting probes can be magnetically isolated at once. By using release probes corresponding to each specific sorting probe, the sorting probes can be selectively unlocked by strand displacement to sort the target cell of interest from the overall population of cells.

The method of using the disclosed DNA-gated sorting system and kit is described in more detail below.

A. Cell Sorting

Cells can be sorted from any biological specimen. Exemplary biological specimen include but are not limited to a cell suspension, a biopsy, tissue, blood, serum, plasma, lymphatic fluid, biological fluid, and tumors. The specimen can be from a human patient or from a laboratory animal, such as rabbits, goats, mice, rats, hamsters, guinea pigs, sheep, dogs, cats, monkeys, chimpanzees, and apes, or from established cell lines. In one embodiment, the biological sample can be from normal tissue, or diseased tissue.

In one embodiment, the biological specimen can be processed into a single-cell suspension prior to DNA-gated cell sorting. Methods of producing a single-cell suspension from a biological specimen are known in the art. Exemplary methods include mechanical homogenization with methods such as sonication, manual pulverization, and high speed enzymatic digestion with enzymes such as collagenase, proteinase K, trypsin, and thermolysin, and acid digestion with HCL. The cell suspension can then be resuspended in an appropriate buffer for magnetic sorting.

After the single-cell suspension of the biological specimen is prepared, sorting probes can be designed. In one embodiment, one sorting probe/release probe pair is associated with one specific cell surface marker. The nucleic acid of the targeting probe is conjugated to an antibody that can target a specific cell surface marker to create a targeting probe (for exemplary purposes targeting probe A ($TP^A$)). The corresponding nucleic acid of the catch probe is conjugated to a magnetic bead to create a catch probe (for exemplary purposes catch probe A ($CP^A$)). In one embodiment, the cell suspension is contacted with the targeting probe before the targeting probe or the cells are contacted with the catch probe. The antibody portion of the targeting probe will bind to the cell surface receptor, creating a complex of target cell and targeting probe. After the cell suspension has been incubated with the targeting probe, the catch probe can be added to the cell suspension. The catch probe will hybridize with the corresponding targeting probe to create a closed DNA-gate. In one embodiment, this creates a complex of target cell, sorting probe and magnetic bead. Once the cell suspension has incubated with the catch probe, the entire suspension can be inserted into a magnetic sorting device. The labeled cells will be captured by the magnetic sorting device.

Magnetic sorting devices are available commercially. Exemplary devices include but are not limited to automated magnetic cell sorters such as autoMACS Pro Separator (Miltenyi Biotec), manual magnetic columns, and manual magnetic separators such as MACSxpress Separator (Miltenyi Biotec) and DynaMag™-2 Magnet (ThermoFisher).

In one embodiment, once the cell suspension including the sorting probes is placed into the magnetic sorting device, the corresponding release probe (for exemplary purposes release probe A ($RP^A$)) is added into the magnetic sorting device. The release probe will hybridize with the toehold domain of the corresponding targeting probe. This will cause a strand-displacement reactions to occur, opening the sorting probe and releasing the catch probe with the magnetic bead from the target cell complex. The target cells can be collected in the flow through from the magnetic sorting device.

In one embodiment, multiple sorting probe/release probe sets can be used with a single biological specimen to sort and collect multiple cell types from one biological specimen. Unlike bead-based sorting methods which require serial labeling and purifying steps to isolate multiple populations of cells from a biological sample, DNA-gated sorting uses a single capture step followed by sequential release steps to sort multiple cell types. The multiple sorting probes can be added to the biological sample simultaneously, for example $TP^A+CP^A$, $TP^B+CP^B$, and $TP^C+CP^C$. The biological sample and sorting probe mixture can be added to the magnetic sorting device. The release probes can then be added one at a time in order to sequentially collect each target cell type. For example, $RP^A$ can be added to the magnetic sorting device, the catch probe will detach from $TP^A$, and cell type A will be released from the magnetic column and collected in the flow through. Target cell types B and C will still be bound to the magnet. $RP^B$ can then be added, the catch probe will detach from $TP^B$, and cell type B will be released from the magnetic column and collected in the flow through. Target cell type C will still be bound to the magnet. $RP^C$ can then be added, the catch probe will detach from $TP^C$, and cell type C will be released from the magnetic column and collected in the flow through.

In another embodiment, multiple sorting probe/release probe sets can be used to sort cells based on more than one cell surface marker, for example sorting double-positive cells. In this embodiment, a single cell can be bound by two or more sorting probes on two or more cell surface markers. The cell will be attached to the magnetic sorting device by means of two or more sorting probes. Therefore, cell type ABC will be fully released from the magnetic sorting device once catch probes A, B, and C have been released from sorting probes A, B, and C by $RP^A$, $RP^B$, and $RP^C$.

In another embodiment, multiple sorting probe/release probe sets can be used on the same biological specimen to sort antigen-specific cells. In this embodiment, one sorting probe can target a specific cell type and subsequent sorting probes can target antigen-specific subtypes of the target cell type. The release probe for the sorting probe labeling the target cell type can be contacted with the cells first, releasing the magnetic probe from the cell specific marker. Then subsequent release probes would release the magnetic probe from the specific antigens on the target cells. In one embodiment, peptide MHC complexes can be targeted for sorting of antigen specific T cells. The breadth of the T cell response and repertoire ($>10^6$ different cell types) requires a highly multiplexed platform which currently cannot be achieved by any other platform. The disclosed sorting kit could potentially sort an exponential number of different cell types, including antigen-specific T cells. Sorting antigen-specific cells can is an important application for monitoring vaccines, cancer immunotherapies and T cell engineering.

One embodiment provides a method of isolating antigen presenting cells. In this embodiment, a heterogeneous population of cells including antigen-presenting cells us contacted with one or more of the disclosed probes for sorting. The binding moiety of the probes includes a T cell receptor complex displaying a peptide antigen. Once the cells are contacted with the probes, cells bounds by the probes are magnetically separated into a sub population of cells, wherein the cells bound by the one or more probes are antigen presenting cells, such as dendritic cells, macrophages, or B lymphocytes.

Also provided is a method of promoting an antigen specific immune response in a subject in need. This method includes isolating immune cells from the subject, sorting the isolated immune cells according to the disclosed cell sorting methods, and administering the isolated cells to the subject to promote an antigen specific immune response in the subject, such as an anti-cancer response, an anti-viral response, or an anti-bacterial response. The sorting can occur ex vivo. The immune response can be the activation of killer T cells 1. Cells to be Sorted The disclosed DNA-gated cell sorting systems and methods can be used to sort and collect cells from a biological specimen. In another embodiment, the disclosed DNA-gated cell sorting systems and methods can be used to remove target cells from a biological specimen and return the biological specimen to the subject. For example, the target cells can be removed from circulating blood or cerebrospinal fluid and the fluids can be returned to the subject without the target cells.

The disclosed DNA-gated cell sorting systems and methods can be used to detect cells in a biological specimen and diagnose a disease or condition. For example, circulating cancer cells, immune cells, or certain proteins or metabolites can be detected in blood or tissue using the disclosed systems and methods and the detection of these cells can indicate a disease state.

Exemplary cells to be detected, sorted, or collected using the disclosed systems and methods are described below.

a. Endogenous Cells

In one embodiment, the disclosed DNA-gated cell sorting systems and methods can be used to sort and collect endogenous cells. Endogenous cells refer to cells that are naturally occurring in an organism. In one embodiment, endogenous cells can include but are not limited to stem cells, immune cells, endothelial cells, epithelial cells, and hematopoietic cells.

In one embodiment, stem cells can be sorted and collected from a biological specimen to be used in stem cell therapy. Stem cells can be adult stem cells or embryonic stem cells. Exemplary embryonic stem cell markers include but are not limited to Oct4, Nanog, Sox2, Sall4, Dax1, Essrb, Tbx3, Tcl1, Rif1, Nac1, Zfp281, TRA1-60, TRA-1-81, Fzd 1-10, TDGF-1, Nestin, GDF-1, Blimp1, Stellar, Fragilis, Piwil2, Dazl, MVH, c-kit, Tekt1, Nanos, and GDF-3.

Exemplary hematopoietic stem cell markers include but are not limited to CD48, CD150, CD244, CD34, CD38, SCA-1, Thy1.1, C-kit, lin, CD135, Slamf1/CD150, Mac-1, and CD4. Exemplary osteoprogenitor cell markers include but are not limited to Gremlin-1, TGF-beta, bFGF, BMP-2, ALPP, MCAM, collagen I, collagen II, RUNX2, decorin, Tpo, alkaline phosphatase, osteocalcin, BAP1, OPN, BAP31, osterix, collagen I, SCUBE3, fibronectin, SPARC, IGFBP3, TGF-beta, RANKL, MCSF, sclerostin, and DKK. Exemplary myogenic precursor cell markers include but are not limited to CD56, CD146, VE-cadherin, alpha-smooth muscle actin, FABP3, integrin alpha 7, desmin, and myosin heavy chain. Exemplary neural stem cell markers include but are not limited to CD133, CD15, CD24, GCTM-2, CD45, nestin, Sox-2, ABCG2, FGF-R4, and Frizzled-9. Exemplary mesenchymal stem cell markers include but are not limited to CD10, CD13, CD73, CD105, CD271, CD140b, HER2/erbB2 (CD340), frizzled-9 (CD349), CD29, CD90, CD146, oct4, and SSEA4. Exemplary skin cell markers include but are not limited to K15, CD34, nestin, follistatin, p63, integrin-alpha 6, tenascin C, EGFR, IGFR, delta1, and TBRII. Exemplary intestinal stem cell markers include but are not limited to gremlin1, Lrig1, Lgr5, Bmi1, Tert, and Hopx.

Exemplary immune cells include but are not limited to B cells, T cells, dendritic cells, lymphoid cells, monocytes, macrophages, myeloid-derived suppressor cells, natural killer cells, platelets, red blood cells. Immune cell markers include but are not limited to T cell markers, such as CD3, CD4, and CD8; B cell markers, such as CD45R/B220, CD19, and CD22; dendritic cell markers, such as CD11c and CD123; NK cell markers such as CD335; stem cell markers, such as CD34; macrophage/monocyte markers such as CD11b/Mac-1 and Ly-71 (F4/80); granulocyte markers such as CD66b, Gr-1/Ly6G, and Ly6C; platelet markers such as CD41, CD61 (Integrin 03), CD9, and CD62P.

In another embodiment, the sorting probes bind to unique T cell receptors or unique B cell receptors.

b. Cancer Cells

In another embodiment, the disclosed DNA-gated cell sorting systems and methods can be used to sort and collect cancer cells. The cancer cells can be circulating cancer cells or cancer cells from a solid tumor. Presence of cancer cells in a biological specimen can be used to diagnose cancer or cancer stage/progression, monitor patient response to cancer treatment, or indicate relapse during follow-up period.

In one embodiment, the sorting probe can specifically bind to a cell surface protein or a protein or peptide secreted into the microenvironment of cell to be treated, for example a cancer cell, tumor cell, or virally infected cell. In some embodiments, the protein or peptide that is specifically recognized by the sorting probe can be cell surface proteins involved in signal transduction, tumor specific antigens, tumor neovasculature antigens, viral proteins or viral peptides displayed in the surface of cells, cytokines, and cytokine receptors. These targeted proteins or peptides may be substances produced by a cell or may be substances which accumulate at a cell microenvironment site, or on cell surfaces.

In one embodiment, the sorting probes specifically bind to PDGF, nucleolin, P-selectin, EpCAM, CD44, Mucin, AXL, PSMA, ICAM-1, VCAM-1, transferrin receptor, ErbB2, VEGFR, HIV-1 Tat protein, HIV Nucleocapsid, integrin, Her3, IL-10, anti-NF-KB, Kanamycin A, catenin, ERK2, C-reactive protein, L-tryptophan, SARS Coronavirus, influenza B, thrombin Hemagglutinin, tumor necrosis factor-alpha, VEGF, streptavidin, Kit-129, HIV Reverse transcriptase, insulin, PSA, RNase H1, Swine influenza A virus, Human neutrophil elastase, anti-IgE, L-selectin, 4-1BB, Tenascin-C, Protein Kinase C, RBP4, Enterotoxin B, her2, Hepatocyte growth factor receptor, Hepatitis C, Fibrogen, HGF, IgG, EGFR, survivin, Osteopontin, P-selectin, neurotrophin receptor, interferon-γ, Human matrix metalloprotease 9, Keratinocyte growth factor, MCP-1, von-Willebrand factor, Plasminogen activator inhibitor-1, OX40, CD4, CD3, CD8, Tenascin-C, androgen receptor (AR), androgen receptor splicing variants (ARV7 (AR3), ARV12, ARV3, ARV1, ARV9, ARV2, ARV5/6, ARV8, ARV9, ARV10, ARV11).

Tumor-associated antigens that can be targeted by the disclosed sorting probes may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene.

Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

Exemplary oncogenes that can be targeted to direct the disclosed compositions to tumors, tumor cells, or tumor microenvironments include, but are not limited to ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.*, 309:883 (1983); Lloyd, et al., *Int. J. Canc.*, 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.*, 36:755 (1997); Sarandakou, et al., *Eur. J Gynaecol. Oncol.*, 19:73 (1998); Meier, et al., *Anticancer Res.*, 17(4B):2945 (1997); Kudoh, et al., *Gynecol. Obstet. Invest.*, 47:52 (1999)). Elevated serum CA125 may also accompany neuroblastoma (e.g., Hirokawa, et al., *Surg. Today*, 28:349 (1998), while elevated CEA and SCC, among others, may accompany colorectal cancer (Gebauer, et al., *Anticancer Res.*, 17(4B):2939 (1997)).

A tumor antigen may include a cell surface molecule. Tumor antigens of known structure and having a known or described function, include the following cell surface receptors: HER1, HER2, HER3, HER4, epidermal growth factor receptor (EGFR), vascular endothelial cell growth factor, vascular endothelial cell growth factor receptor, insulin-like growth factor-I, insulin-like growth factor-II, transferrin receptor, estrogen receptor, progesterone receptor, follicle stimulating hormone receptor (FSH-R), retinoic acid receptor, MUC-1, NY-ESO-1, NA 17-A, Melan-A/MART-1, tyrosinase, Gp-100, MAGE, BAGE, GAGE, any of the CTA class of receptors including in particular HOM-MEL-40 antigen encoded by the SSX2 gene, carcinoembryonic antigen, and p97 (melanotransferrin). Additional tumor associated antigens include prostate surface antigen (PSA); s-human chorionic gonadotropin (β-HCG); glycosyltransferase β-1,4-N-acetylgalactosaminyltransferases (GalNAc); NUC18; melanoma antigen gp75; human cytokeratin 8; high molecular weight melanoma antigen. CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferase AS fusion protein, HLA-A2, HLA-A1, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4, 5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p5(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70\K, NY-CO-1, RCAS1, SDCCAGi6, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

The targeted antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed fusion proteins.

In another embodiment the sorting probes specifically bind to target antigens selected from the group consisting of carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, PSMA, CEACAM5, CEACAM6, c-met, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, PLAGL2, and an oncogene product.

In another embodiment, the disclosed DNA-gated sorting system can be used to sort and detect cancer stem cells. Markers for cancer stem cells include but are not limited to CD44, CD133, CD24, CD90, CD271, CD49f, CD13, CK5, CK10, CK15, CK8, CK18, CK14, and ALDH1.

e. Diseased Cells

The disclosed DNA-gated cell sorting systems and methods ca be used to sort, collect, or remove diseased cells from a biological specimen more specifically a biological fluid. Diseased cells can be detected by aberrant cell surface markers. Exemplary diseased cells include but are not limited to sickled blood cells, virally infected cells, bacterially infected cells, and fungally infected cells.

i. Viral Cells

The disclosed DNA-gated cell sorting systems and methods can be used to sort and collect viral cells or cells infected by viral cells.

In some embodiments, the sorting probe binds a viral protein selected from the group consisting of a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

B. Proteins

In addition to sorting whole cells, the disclosed DNA-gated cell sorting systems and methods can be used to sort and detect circulating proteins, peptides or protein fragments. The sorting probe can bind to any circulating proteins, peptides, or protein fragments. Exemplary proteins involved in disease and disease progression are described below.

Proteins involved in cardiovascular diseases include but are not limited to BNP, N-terminal prohormone of brain natriuretic peptide [NT-proBNP], atrial natriuretic peptide [ANP], ST-2, troponin T or I, creatinine phosphokinase-MB, copeptin, high sensitivity Troponin, galectin-3, C-reactive protein, interleukin 6, Fibrinogen, monocyte chemotactic protein-1, tumor necrosis factor alpha, lipoprotein (a), low-density lipoproteins, high density lipoprotein, ApoB 100, Lipoprotein-associated phospholipase A2, Homocysteine, vitamin D, fibroblast growth factor 23, adiponectin, glycated hemoglobin, and haptoglobin.

Exemplary proteins involved in gastrointestinal diseases include but are not limited to immunoglobulins, mucins, GUC2AB, PDZD3, fibronectin 1, retinol-binding protein 2 (RBP2), tight junction proteins such as occludin and claudin, VIP, P2RY4, guanylyl cyclase C receptor, uroguanylin, guanylin, serotonin reuptake protein (SERT), calprotectin, and human beta-defensin 2.

Exemplary proteins involved in liver disease include but are not limited to alanine aminotransferase (ALT), aspartate aminotransferase (AST), cleaved cytokeratin 18, MDA, SOD, CAT, and GPx.

In another embodiment, the sorting probe can specifically binds to a chemokine or a chemokine receptor. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are important for tumor progression.

Based on the positioning of the conserved two N-terminal cysteine residues of the chemokines, they are classified into four groups namely CXC, CC, CX3C and C chemokines. The CXC chemokines can be further classified into ELR+ and ELR− chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

In one embodiment, tumor or tumor-associated neovasculature targeting domains are ligands that bind to cell surface antigens or receptors that are specifically expressed on tumor cells or tumor-associated neovasculature or are overexpressed on tumor cells or tumor-associated neovasculature as compared to normal tissue. Tumors also secrete a large number of ligands into the tumor microenvironment that affect tumor growth and development. Receptors that bind to ligands secreted by tumors, including, but not limited to growth factors, cytokines and chemokines, including the chemokines provided above, are suitable for use in the disclosed fusion proteins. Ligands secreted by tumors can be targeted using soluble fragments of receptors that bind to the secreted ligands. Soluble receptor fragments are fragments polypeptides that may be shed, secreted or otherwise extracted from the producing cells and include the entire extracellular domain, or fragments thereof.

C. Metabolites and Enzymes

The disclosed DNA-gated cell sorting systems and methods can be used to sort and detect metabolites or enzymes in a biological specimen. Because multiple sorting probe/release probe sets can be used on one biological specimen, an entire metabolic panel could be run using one biological sample.

Exemplary metabolites and enzymes that can be detected include but are not limited to elastase, 5-Hydroxy-Indol Acetic Acid, lactic dehydrogenase, neuron specific enolase, NMP22, prostatic acid phosphatase, vanillylmandelic acid, homovanillic acid, short chain fatty acids include propionate, butyrate, and acetate, arginine, propionycarnitine, lysophosphatidylcholine, serotonin, spermidine, sphingomyelin, hydroxysphingomyelin, lactic acid, alanine aminotransferase, albumin, alkaline phosphatase, aspartate aminotransferase, bilirubin, creatinine, calcium, globulin, glucose, potassium, and sodium.

D. Logic-Based Sorting

The disclosed DNA-gate/release probe sets can be used for logic based sorting. In one embodiment, cells can be sorted based on the presence or absence of cell surface markers. Logic based sorting can use sorting gates such as [AND] gates and [OR] gates. Logic based sorting can be used to analyze different populations of a single cell type, for example, subsets of T cells. In a biological sample having DNA-gate A, DNA-gate B, DNA-gate C, and DNA-gate D, logic gates can be established for cells having DNA-gate A [AND] DNA-gate B, DNA-gate A [AND] DNA-gate C, or DNA-gate A [OR] DNA-gate D.

In one embodiment, a heterogeneous cell population can be interrogated for specific expression patterns of cell surface molecules and separated into different aliqouts wherein the cells of each aliquot express a different expression pattern for the cell surface molecules. This application of the disclosed probes is referred to as DNA logic gates. For example, cells can be sorted from a heterogeneous cell population into separate aliquots of isolated cells that express molecules A and B but not C in one aliquot, cells that express A and C but not B can be isolated in a second aliquot, express B and C but not A in a third aliquot, express A but not B and C in a fourth aliquot, express C but not A and B in a fifth aliquot, and so on. The application of logic gates is not limited by number and can interrogate at least 2, 3, 4, 5, 6, 7, 8, 9, 10, 20, 30, 40, 50, 60, 60, 80, 90, 100, 1000, 10,000, 100,000, 1,000,000 or more cell surface molecule on all possible combinations of expression or lack of expression. Multiple layers of release probes can be applied to a single heterogeneous cell population in order to sort the population into various subsets of cells. In one embodiment a single heterogeneous cell population can be separated into subsets of T cells that are activated and express both CD8+/CD44+, exhausted T cells that are CD8+/PD-1+, antigen-specific T cells that are CD8+/pMHC+, and other subpopulations of cells as desired. In another embodiment, a single heterogeneous population can be separated into subsets of T cells expressing CD8 and FoxP3 or T cells expressing CD8 but not expressing FoxP3.

One embodiment provides a method of sorting a heterogeneous population of cells into subsets of cells having unique cell surface molecule expression patterns. In this embodiment, a heterogeneous population of cells, for example immune cells, is contacted with one or more of the disclosed probes for cell sorting. Each probe is designed to bind to a different cell surface molecule, including but not limited to cell surface proteins, cell surface receptors, ligand for cell surface receptors, lectins, polysaccharides, and combinations thereof. Once the probes are allowed to bind to the cell surface molecules that may be present on the cells in the heterogeneous population, the labeled cells are magnetically sorted into a first subset of cells that express a subset of the cell surface molecules bound by the one or more probes and a second subset of cells that do not express the cell surface molecules and are not bound by the probes. The cells that are not bound by the probes do not express the cell surface molecule recognized by the probe. In this embodiment, the second subset of cells is then contacted with N number of probes wherein each of the N number of probes specifically binds to a unique cell surface molecule. The cells labeled with the N number of probes are then magnetically sorted to isolate cells having a desired expression pattern of cell surface markers by contacting the cells from the previous step with one or more release probes that specifically anneal to the N number of probes that bind the cell surface molecules of the desired expression pattern. The released cells are isolated from the cells bound by the probes having magnetic beads. The isolated cells contacted with the N number of probes do not express the cell surface molecule bound by the one or more probes and do express the desired expression pattern of cell surface markers bound by the N number of probes.

In one embodiment the method further includes the steps of contacting the first subset of cells with the N number of probes wherein each of the N number of probes specifically binds to a unique cell surface molecule, and isolating cells contacted with the N number of probes having a desired expression pattern of cell surface markers by contacting the cells from step with one or more release probes that specifically anneal to the N number of probes that bind the cell surface molecules of the desired expression pattern.

In one embodiment a library of cell sorting probes can be created. In this embodiment, a plurality of cell sorting probes and a plurality of release probes can be designed. Each sorting probe/release probe set can be unique to a specific cell surface marker or receptor. The library of cell sorting probes can be applied to recognize 2, 3, 4, 5, 6, 7, 8, 9, 10, 20, 30, 40, 50, 60, 60, 80, 90, 100, 1000, 10,000, 100,000, 1,000,000 or more cell surface markers or molecules.

E. Biomedical Applications

The disclosed DNA-gated cell sorting systems offer a more efficient method of cell sorting with the ability to detect an unlimited amount of cell surface markers in one biological sample. DNA-gated cell sorting can be used for a variety of biomedical applications. Exemplary applications of DNA-gated sorting include but are not limited to cancer diagnosis and prognosis, immunological disease diagnosis and prognosis, purification of specific cell populations for cell-based therapies, the detection and collection of cancer stem cell markers, and monitoring polyclonal patient immune response to vaccines.

The disclosed systems and methods can be used to remove diseased cells from biological fluids such as blood or cerebrospinal fluids. In another embodiment, the disclosed systems and methods can be used to remove cells from the body and expand them ex vivo before replacing them into the subject. Exemplary methods of removing cells and expanding of modifying the cells ex vivo includes but is not limited to stem cell therapy and CAR-T cells therapy. The disclosed systems and methods can be used for adoptive cell transfer and mapping cellular differentiation pathways.

The disclosed DNA-gated sorting systems could also be used in research laboratory settings instead of traditional flow cytometry and fluorescence based sorting.

EXAMPLES

Example 1. Engineering Dynamic Antibody DNA Gates

Methods and Materials
DNA Sequence Design:

TP, CP, and RP strand sequences were designed in silico using a domain-based approach. To generate TP strands, pools of 6 nt toehold domain and 20 nt hybridization domain sequences each containing 50% GC content were generated and checked for minimal secondary structure (i.e. little to no intramolecular binding) at 25° C. using NUPACK software. After filtering out oligos with significant structure, each remaining toehold domain was concatenated to the 5' end of a hybridization domain, and lack of secondary structure was again verified in silico. Corresponding CP and RP strands were generated by taking the reverse complement of the hybridization domain or the entire TP strand, respectively. Orthogonality between gates was checked by inputting TP and CP sequences for all gates with and without all RP sequences and analyzing the resulting species at equilibrium as predicted by NUPACK. See Tables 1 and 2 for exemplary DNA gate sequences that were designed herein.

TABLE 1

DNA gate sequences A-C[1]

| ID | Sequence | SEQ ID NO: |
|---|---|---|
| *Sequences for kinetic studies and testing displacement on cell surfaces* | | |
| TP$^A$ | 5' NH2-GGA ACT TAA CTG GGC GCA CGA TCT AT-Cy5 3' | 1 |
| CP$^A$ | 5' 1 AbRQ-ATA GAT CGT GCG CCC AGT TA 3' | 2 |
| RP$^A$ | 5' ATA GAT CGT GCG CCC AGT TAA GTT CC 3' | 3 |
| TP$^B$ | 5' NH2-GTC TCA GTC TCA GTG GCG TAA TAA CC-Cy5 3' | 4 |

TABLE 1 -continued

DNA gate sequences A-C[1]

| ID | Sequence | SEQ ID NO: |
|---|---|---|
| CP$^B$ | 5' IAbRQ-GGT TAT TAC GCC ACT GAG AC 3' | 5 |
| RP$^B$ | 5' GGT TAT TAC GCC ACT GAG ACT GAG AC 3' | 6 |
| TP$^C$ | 5' NH2-GGT CAT GGG GCT ATA ACA ACG TCT CT-Cy5 3' | 7 |
| CP$^C$ | 5' IAbRQ-AGA GAC GTT GTT ATA GCC CC 3' | 8 |
| RP$^C$ | 5' AGA GAC GTT GTT ATA GCC CCA TGA CC 3' | 9 |
| *Sequences for multiplexed cell sorting* | | |
| TP$^A$ | 5' NH2-GGA ACT TAA CTG GGC GCA CGA TCT AT 3' | 10 |
| CP$^A$ | 5' BiotinTEG-AAA AAA AAA AAT AGA TCG TGC GCC CAG TTA 3' | 11 |
| RP$^A$ | 5' ATA GAT CGT GCG CCC AGT TAA GTT CC 3' | 12 |
| TP$^B$ | 5' NH2-GTC TCA GTC TCA GTG GCG TAA TAA CC 3' | 13 |
| CP$^B$ | 5' BiotinTEG-AAA AAA AAA AGG TTA TTA CGC CAC TGA GAC 3' | 14 |
| RP$^B$ | 5' GGT TAT TAC GCC ACT GAG ACT GAG AC 3' | 15 |
| TP$^C$ | 5' NH2-GGT CAT GGG GCT ATA ACA ACG TCT CT 3' | 16 |
| CP$^C$ | 5' BiotinTEG-AAA AAA AAA AAG AGA CGT TGT TAT AGC CCC 3' | 17 |
| RP$^C$ | 5' AGA GAC GTT GTT ATA GCC CCA TGA CC 3' | 18 |

[1]Toeholds in TP strands are underline.
[2]Domain sequences are identical to those used in the kinetic studies. However, the fluorophore and quencher are removed from TP and CP strands, respectively, and CP strands are derivatized with biotin and a poly(A)$_{10}$ region.

TABLE 2

DNA gate sequences α-ω.

| | | Sequences for multiplexed cell sorting | SEQ ID NO: |
|---|---|---|---|
| Gate α | TP | 5' NH2-GAG TTG GAG AGT TGT GAG GGA GTA TG 3' | 19 |
| | CP | 5' BiotinTEG-AAA AAA AAA ACA TAC TCC CTC ACA ACT CTC 3' | 20 |
| | RP | 5' CAT ACT CCC TCA CAA CTC TCC AAC TC 3' | 21 |
| Gate β | TP | 5' NH2-GTT GAG GTG AGA TGG AAG GAT GTT GG 3' | 22 |
| | CP | 5' BiotinTEG-AAA AAA AAA AAC CAA CAT CTT CCA TCT CAC 3' | 23 |
| | RP | 5' CCA ACA TCC TTC CAT CTC ACC TCA AC 3' | 24 |

TABLE 2-continued

DNA gate sequences α–ω.

| | | Sequences for multiplexed cell sorting | SEQ ID NO: |
|---|---|---|---|
| Gate γ | TP | 5' NH2-GTG TAG GGA GGG TTG TAG TAG GAA TG 3' | 25 |
| | CP | 5' BiotinTEG-AAA AAA AAA ACA TTC CTA CTA CAA CCC TCC 3' | 26 |
| | RP | 5' CAT TCC TAC TAC AAC CCT CCC TAC AC 3' | 27 |
| Gate δ | TP | 5' NH2-GAT GTG GGT GGT GTA ATG AGT GAG AG 3' | 28 |
| | CP | 5' BiotinTEG-AAA AAA AAA ACT CTC ACT CAT TAC ACC ACC 3' | 29 |
| | RP | 5' CTC TCA CTC ATT ACA CCA CCC ACA TC 3' | 30 |
| Gate ε | TP | 5' NH2-GGA TAG GTG GAG AAG GTT GAG GTT AG 3' | 31 |
| | CP | 5' BiotinTEG-AAA AAA AAA ACT AAC CTC AAC CTT CTC CAC 3' | 32 |
| | RP | 5' CTA ACC TCA ACC TTC TCC ACC TAT CC 3' | 33 |
| Gate ζ | TP | 5' NH2-GTA AGG GTG TAG GTG A AT AGG TGG AG 3' | 34 |
| | CP | 5' BiotinTEG-AAA AAA AAA ACT CCA CCT ATT CAC CTA CAC 3' | 35 |
| | RP | 5' CTC CAC CTA TTC ACC TAC ACC CTT AC 3' | 36 |
| Gate η | TP | 5' NH2-GTG AAG GAG TGA GTG AGG TTA AGT GG 3' | 37 |
| | CP | 5' BiotinTEG-AAA AAA AAA ACC ACT TAA CCT CAC TCA CTC 3' | 38 |
| | RP | 5' CCA CTT AAC CTC ACT CAC TCC TTC AC 3' | 39 |
| Gate θ | TP | 5' NH2-GAG ATG GGA TAA GTA GGT GTG GGT AG 3' | 40 |
| | CP | 5' BiotinTEG-AAA AAA AAA ACT ACC CAC ACC TAC TTA TCC 3' | 41 |
| | RP | 5' CTA CCC ACA CCT ACT TAT CCC ATC TC 3' | 42 |
| Gate ι | TP | 5' NH2-GAA GTG GTG GTT AGG AAG TGA GAG TG 3' | 43 |
| | CP | 5' BiotinTEG-AAA AAA AAA ACA CTC TCA CTT CCT AAC CAC 3' | 44 |
| | RP | 5' CAC TCT CAC TTC CTA ACC ACC ACT TC 3' | 45 |
| Gate κ | TP | 5' NH2-GTA GTG GTG AAA TGG TAT GGG TGG AG 3' | 46 |
| | CP | 5' BiotinTEG-AAA AAA AAA ACT CCA CCC ATA CCA TTT CAC 3' | 47 |
| | RP | 5' CTC CAC CCA TAC CAT TTC ACC ACT AC 3' | 48 |
| Gate λ | TP | 5' NH2-GTA TGG GTG TGG TGT AGA ATG GAG AG 3' | 49 |
| | CP | 5* BiotinTEG-AAA AAA AAA ACT CTC CAT TCT ACA CCA CAC 3' | 50 |
| | RP | 5' CTC TCC ATT CTA CAC CAC ACC CAT AC 3' | 51 |
| Gate μ | TP | 5' NH2-GGT AAG GTG AGA GGA GTA GGT ATG TG 3' | 52 |
| | CP | 5' BiotinTEG-AAA AAA AAA ACA CAT ACC TAC TCC TCT CAC 3- | 53 |
| | RP | 5' CAC ATA CCT ACT CCT CTC ACC TTA CC 3' | 54 |
| Gate ν | TP | 5' NH2-GAG TAG GTG TGG GAA GTA GGT GTA AG 3' | 55 |
| | CP | 5' BiotinTEG-AAA AAA AAA ACT TAC ACC TAC TTC CCA CAC 3' | 56 |
| | RP | 5' CTT ACA CCT ACT CCA CAC CTA CTC 3' | 57 |
| Gate ξ | TP | 5' NH2-GTG ATG GGT AGG GTT GAT TGG GAA AG 3' | 58 |
| | CP | 5' BiotinTEG-AAA AAA AAA ACT TTC CCA ATC AAC CCT ACC 3' | 59 |
| | RP | 5' CTT TCC CAA TCA ACC CTA CCC ATC AC 3' | 60 |

TABLE 2-continued

DNA gate sequences α-ω.

| | | Sequences for multiplexed cell sorting | SEQ ID NO: |
|---|---|---|---|
| Gate ο | TP | 5' NH2-GTA GAG GGA GAG TAT TGT AGA GGT GG 3' | 61 |
| | CP | 5' BiotinTEG-AAA AAA AAA ACC ACC TCT ACA ATA CTC TCC 3' | 62 |
| | RP | 5' CCA CCT CTA CAA TAC TCT CCC TCT AC 3' | 63 |
| Gate π | TP | 5' NH2-GAT AGG GTA AGA ATG GGA GTT GGT GG 3' | 64 |
| | CP | 5' BiotinTEG-AAA AAA AAA ACC ACC AAC TCC CAT TCT TAC 3' | 65 |
| | RP | 5' CCA CCA ACT CCC ATT CTT ACC CTA TC 3 | 66 |
| Gate ρ | TP | 5' NH2-GAT TGG GAT GGT AGG GAG TGT AGA TG 3' | 67 |
| | CP | 5' BiotinTEG-AAA AAA AAA ACA TCT ACA CTC CCT ACC ATC 3' | 68 |
| | RP | 5' CAT CTA CAC TCC CTA CCA TCC CAA TC 3' | 69 |
| Gate σ | TP | 5' NH2-GGT ATG GTG GAG AGT GTG AAA GGT TG 3' | 70 |
| | CP | 5' BiotinTEG-AAA AAA AAA ACA ACC TTT CAC ACT CTC CAC 3' | 71 |
| | RP | 5' CAA CCT TTC ACA CTC TCC ACC ATA CC 3' | 72 |
| Gate τ | TP | 5' NH2-GAT GAG GAT GGA TGA GGT GAT TGA GG 3' | 73 |
| | CP | 5' BiotinTEG-AAA AAA AAA ACC TCA ATC ACC TCA TCC ATC 3' | 74 |
| | RP | 5' CCT CAA TCA CCT CAT CCA TCC TCA TC 3' | 75 |
| Gate υ | TP | 5' NH2-GGA ATG GTT GGG TGA GAG TAG AAG TG 3' | 76 |
| | CP | 5' BiotinTEG-AAA AAA AAA ACA CTT CTA CTC TCA CCC AAC 3' | 77 |
| | RP | 5' CAC TTC TAC TCT CAC CCA ACC ATT CC 3' | 78 |
| Gate φ | TP | 5' NH2-GGT TAG GGT TTA GAT GAG TGG GAA GG 3' | 79 |
| | CP | 5' BiotinTEG-AAA AAA AAA ACC TTC CCA CTC ATC TAA ACC 3' | 80 |
| | RP | 5' CCT TCC CAC TCA TCT AAA CCC TAA CC 3' | 81 |
| Gate χ | TP | 5' NH2-GAA TGG GAT AAG TTG GGA GTG GGT AG 3' | 82 |
| | CP | 5' BiotinTEG-AAA AAA AAA ACT ACC CAC TCC CAA CTT ATC 3' | 83 |
| | RP | 5' CTA CCC ACT CCC AAC TTA TCC CAT TC 3' | 84 |
| Gate ψ | TP | 5' NH2-GGA TTG GGA TAG TGA A AT GGT GTG GG 3' | 85 |
| | CP | 5' BiotinTEG-AAA AAA AAA ACC CAC ACC ATT TCA CTA TCC 3' | 86 |
| | RP | 5' CCC ACA CCA TTT CAC TAT CCC AAT CC 3' | 87 |
| Gate ω | TP | 5' NH2-GTT AGG GAT GGA ATG GTT AGG AGG TG 3' | 88 |
| | CP | 5' BiolinTEG-AAA AAA AAA ACA CCT CCT AAC CAT TCC ATC 3' | 89 |
| | RP | 5' CAC CTC CTA ACC ATT CCA TCC CTA AC 3' | 90 |

DNA Conjugation to Antibodies and Streptavidin:

Recombinant streptavidin expressing a C-terminal cysteine residue (StvC) was expressed and purified as previously described (Sano T. and Cantor C R, *Proc Natl Acad Sci USA*, 87:142-146 (1990)). Antibodies were reacted with 50-fold excess S-HyNic (Solulink), StvC was reduced with 10 mM TCEP and then reacted with 50-fold excess MHPH (Solulink), and amine-terminated DNA was reacted with 20-fold excess S-4FB (Solulink) for 4 hours. Excess linker was removed by buffer exchanging into citrate buffer (50 mM sodium citrate, 150 mM NaCl, pH 6) using Amicon spin filters (Millipore). Functionalized DNA was combined with antibodies or StvC at a 20:1 or 1:1 ratio, respectively, and reacted overnight. Ab-DNA gates were purified on a Superdex 200 Increase 10/300 GL column using an AKTA Pure FPLC (GE Healthcare). StvCDNA gates were purified using Pierce Spin Columns (Thermo) packed with iminobiotin agarose (Thermo) according to manufacturer's instructions. Conjugation was verified by SDS-PAGE followed by Coomassie staining.

Antibody DNA-Gated Cell Sorting:

All animal work was approved by the Georgia Tech Institutional Animal Care and Use Committee. Each cell sorting reaction started with 5×106 C57BL/6J splenocytes resuspended in 100p sorting buffer (1×PBS+0.1% BSA+2 mM EDTA). Cells were blocked with anti-mouse CD16/CD32 (Mouse BD Fc Block) before staining with 1 µg Ab-TP conjugate for 30 min on ice. 250 pmol biotinylated CP strands were reacted with 1×107 Dynabeads Biotin Binder (Invitrogen) for 15 min at RT before quenching with 50-125 µM d-biotin (Avidity). CP-coated beads were washed 5 times with sorting buffer using a MACSxpress Separator (Miltenyi Biotec) and then annealed to Ab-TP stained cells for 30 min at 4° C. Cell samples were washed 5 times with sorting buffer using the MACSxpress Separator to remove unlabeled cells. Target cells were first released by adding RP strands (5 µM final concentration) to cells resuspended in 500 µl sorting buffer and incubating in a tube rotator for 1 hr at RT and then recovered by washing 5 times with sorting buffer in the MACSxpress Separator. For multiplexed sorts, subsequent RP strand incubation and magnetic washes were performed to recover additional target cell populations. Annealing and release of magnetic beads were visualized by imaging cells using an EVOS FL Auto Imaging System (40× objective, Life Technologies) before and after addition of RP strands. Target cell purity was measured by staining recovered cells with alternate antibody clones against the targeted cell surface marker and analyzing on a BD Accuri C6.

Dual Gated DNA-Gated Cell Sorting with pMHC Tetramers:

Splenocytes from pooled pmel and P14 mice or LCMV Arm infected mice (day 8 p.i.) were CD8 purified by positive or negative selection, respectively, using Ab-DGS as described above. For DGS using pMHC tetramers, 250 pmol biotinylated CP strands were reacted with 1×107 Dynabeads Biotin Binder (Invitrogen) for 15 min at RT and then washed 8 times with sorting buffer using a DynaMag-2 magnet (Invitrogen). 5 µg of corresponding StvC-TP was mixed with appropriate CP-coated beads for 30 min at 4° C. and then washed 5 times with sorting buffer. Next, 18 µg of biotinylated pMHC monomer (Db-GP33 for P14, Db-GP100 for pmel, or Db-GP276, Kb-NP205 for LCMV experiments) was added to StvC-coated beads for 30 min at 4° C. and then washed 5 times with sorting buffer. CD8+ purified cells were then incubated with pMHC tetramer-coated beads for 30 min at 4° C., washed 5 times with sorting buffer to remove unlabeled cells, and then serially incubated with 5 µM appropriate RP strands for 1 hr at RT to recover target antigen-specific cells. Purity was measured by staining released cells with fluorescent tetramer.

Software and Statistical Analysis:

Graphs were plotted and Student's t tests were conducted using GraphPad Prism 6.0. Brightness/contrast of microscopy images were adjusted using ImageJ (NIH). Flow cytometry data were analyzed using FlowJo X.

Results

Figure 3A:
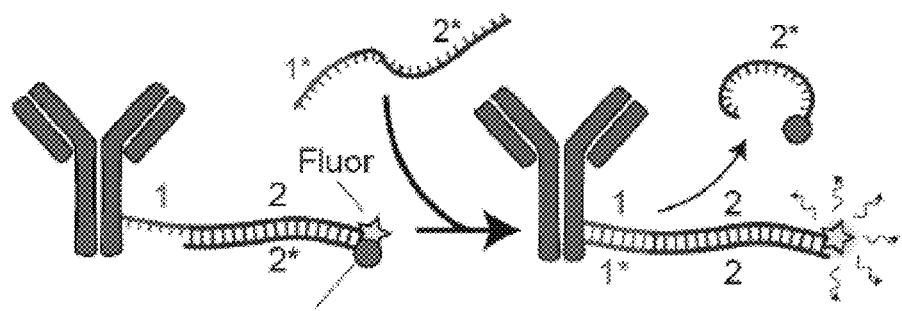
FIG. 3A is a schematic illustration of Ab-DNA complexes used in kinetic studies.
Figure 3B:
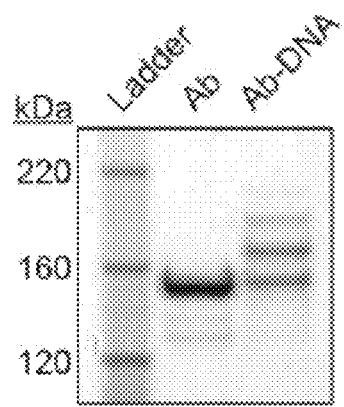
FIG. 3B is an SDS-PAGE of Ab-TP:CP complexes. Multiple DNA complexes were conjugated per antibody.
Figures 3C, 3D, 3E:
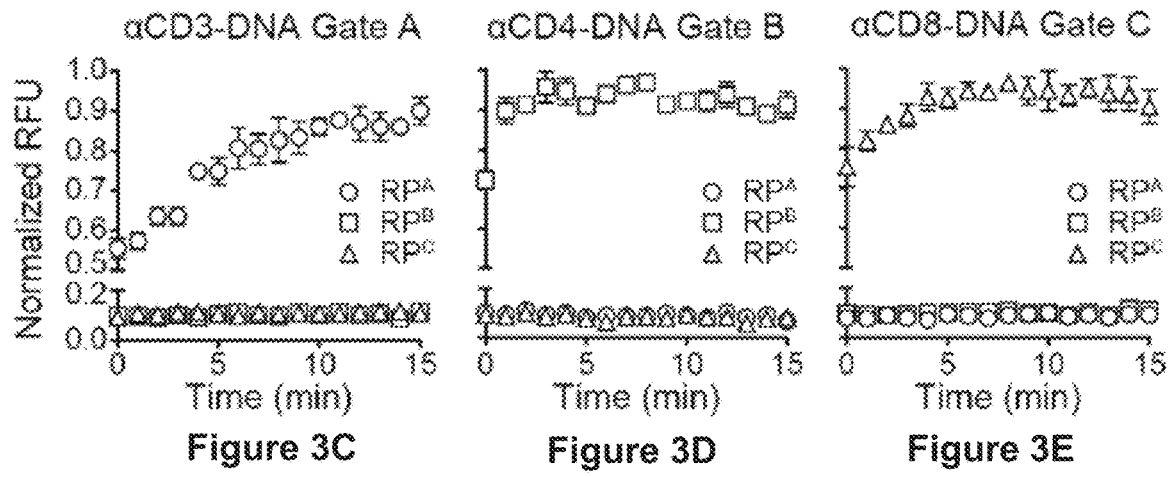
FIGS. 3C-3E are kinetic graphs of DNA strand displacement on antibodies for anti-CD3-DNA Gate A (FIG. 3C), anti-CD4-DNA Gate B (FIG. 3D) and anti-CD8-DNA Gate C (FIG. 3E). Complete displacement occurred within 10 minutes when RP from a matching gate was added (n=3).

DNA sequences (targeting probes (TPs), catch probes (CPs), and release probes (RPs)) were designed in silico for orthogonal DNA gates using a domain-based approach (Bendall, S C, et al., Trends Immunol, 33:323-332 (2012)), where 6 base toehold and 20 base hybridization domains are independently optimized (50% GC content, 5' G/C on the toehold domain). These domains were then concatenated to form candidate TP sequences that were screened in silico using NUPACK (Jaye, D L, et al., J Immunol, 188:4715-4719 (2012)) to minimize secondary structures and cross-hybridization under relevant conditions for sorting (4-25° C., 150 mM NaCl). Using this approach, libraries of 3 (A-C) (Table 1) and 24 gates (α-ω) (Table 2) were designed. Orthogonality and kinetics of DNA displacement were validated by annealing fluorescently labeled TPs with quencher-labeled CPs and incubating complexes with RP from each gate. Displacement was observed within 5 minutes only when TP:CP complexes were reacted with RP strands from matching gates (FIGS. 2A-2C). DNA strand displacement reactions occurring on the surface of antibodies were validated, as the presence of a protein could sterically shield the toehold region from an RP. Antibodies against the cell surface markers CD3, CD4, and CD8 were conjugated with quenched TP:CP conjugates from Gates A, B, and C, respectively (FIG. 3A), and analyzed the resulting products by a mobility shift assay (FIG. 3B). Each antibody-TP:CP complex was incubated with RP strands from its matching gate and observed complete displacement within 5-10 minutes (FIGS. 3C-3E).

Example 2. High Performance Cell Isolation by Strand Displacement

Methods and Materials

DNA-gated antibodies were integrated with magnetic beads to allow selective cell isolation en masse. To do so, the kinetic efficiency of DNA strand displacement on the surface of cells was examined. Three human T cell lines—Jurkat, CCRF-CEM, and TALL-104—as representative of CD3+, CD4+, and CD8+ cells were stained with one of the quenched Ab-TP:CP conjugates (αCD3-TPA:CPA, αCD4-TPB:CPB, and αCD8-TPC:CPC, respectively), and baseline fluorescence on cells by flow cytometry was measured (FIGS. 4A-4D). After incubating cells with RP strands from the matching gate (RPA, RPB, or RPC) to trigger strand displacement, an increase in fluorescent intensity was observed on all three cell types, indicating that strand displacement was preserved on the surface of cells. The use of Ab-DNA gates to label target cells with magnetic beads followed by the reversible release of beads for target cell recovery was tested. Mouse CD8+ T cells were stained with anti-mouse CD8 conjugated with $TP^A$, incubated stained T cells with $CP^A$-labeled magnetic beads, and then looked for bead-bound cells by microscopy.

Results

Figures 4A, 4B, 4C, 4D:
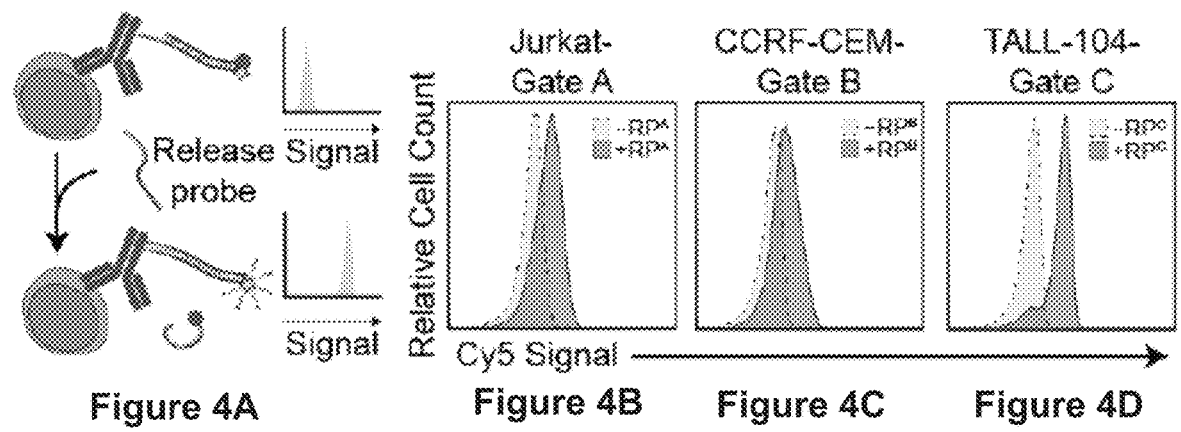
FIGS. 4A-4D show data from CD3+ Jurkat cells, CD4+ CCRF-CEM cells, and CD8+ TALL-104 cells quenched with anti-CD3-$TP^A$:$CP^A$, anti-CD4-$TP^B$:$CP^B$, and anti-CD8-$TP^C$:$CP^C$ complexes.
Figure 4E:
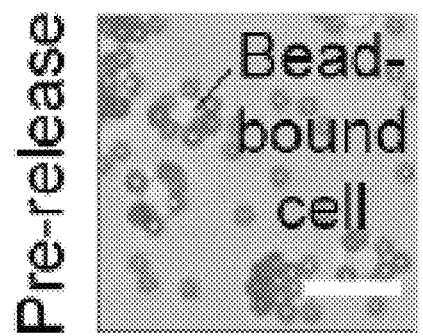
FIGS. 4E-4F are Brightfield images of target cells magnetically labeled by annealing CP-coated magnetic beads (FIG. 4E). After addition of RP strands, beads were released from the cell surface (FIG. 4F).
Figure 4F:
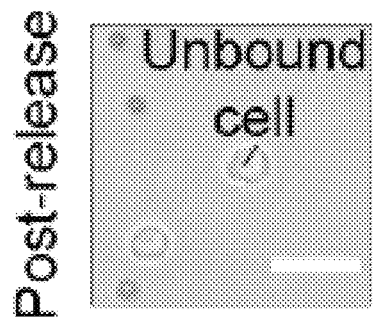
Figure 4G:
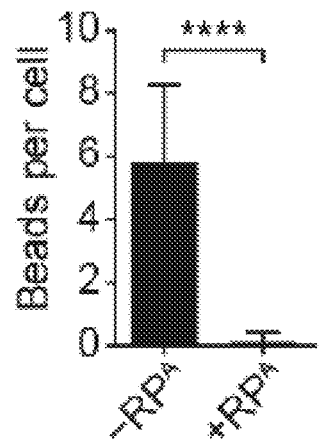
FIG. 4G is a bar graph showing quantification of beads per cell before and after addition of release probe.

Annealing of $TP^A$ and $CP^A$ strands bound beads to cells resulted in an average of 5.8 beads per cell (FIGS. 4E-4G). After incubating bead-bound cells with RPA, the magnetic beads were released from the surface of cells with high efficiency (0.1 beads/cell, ****$p<0.0001$ by unpaired t test). These results show that cells expressing a target cell surface marker can be magnetically captured via DNA hybridization and released by DNA gates.

Figure 4H:
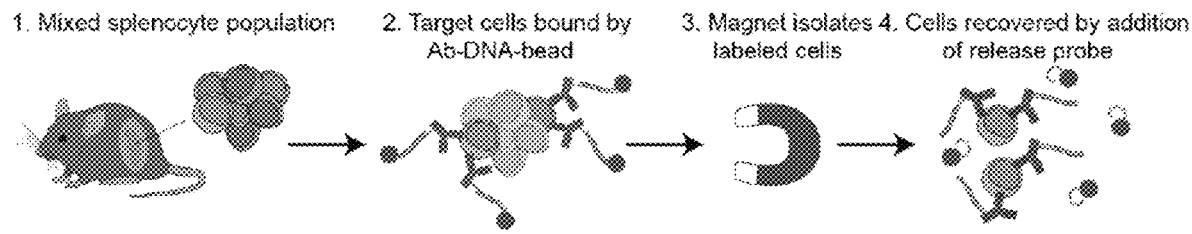
FIG. 4H is a schematic showing the workflow of isolating CD8+ target cells from CD57BL/6J mice by DGS.

DGS was applied to isolate cell populations from a complex biological sample and DGS sorting efficiency was compared to magnetic activated cell sorting (MACS), a commercial platform that is routinely used for cell enrichment. As a testbed, CD8+ T cells were isolated from a mouse spleen because splenocytes are comprised of multiple immune cell populations, including CD8+ and CD4+ T cells, B cells, monocytes, and dendritic cells (FIG. 4H). Splenocytes from C57BL/6J mice were stained with anti-mouse CD8-TPA and then annealed with CPA-coated magnetic beads to labeled CD8+ cells. After capturing target cells in a magnetic column to separate the unbound CD8-depleted fraction, RPA strands were added to displace beads and isolate CD8+ cells. Both the unbound cell fraction and recovered target cells were stained to check for CD8+ cell frequency, finding that DGS enriched CD8+ target cells to a purity >97% with ~90% recovery (CD8+ frequency decreased from 28.7% in the unsorted sample to 2.97% in the unbound fraction) (FIGS. 4I-4J). To measure the performance of sorting with our DNA-gated antibodies, DGS was benchmarked against sorting with a commercial CD8+ positive selection MACS kit and no significant difference was found in several key parameters including CD8+ purity (DGS: 97.1% vs. MACS: 98.1%, p=0.17 by unpaired t test, n=3), cell viability (DGS: 84.0% vs. MACS: 74.6%, p=0.21 by unpaired t test, n=3), and yield (DGS: 4.19×105 cells vs. MACS: 3.81×105 cells, p=0.18 by unpaired t test, n=3) (FIGS. 4L-4N, FIGS. 5A-5L). These results demonstrate that the cell sorting efficiency of DGS from complex cell samples is equivalent to that of commercial platforms.

Example 3. Multiplexed DGS of Murine Splenocytes Preserves Key Cell Functions

Methods and Materials

Figure 6A:
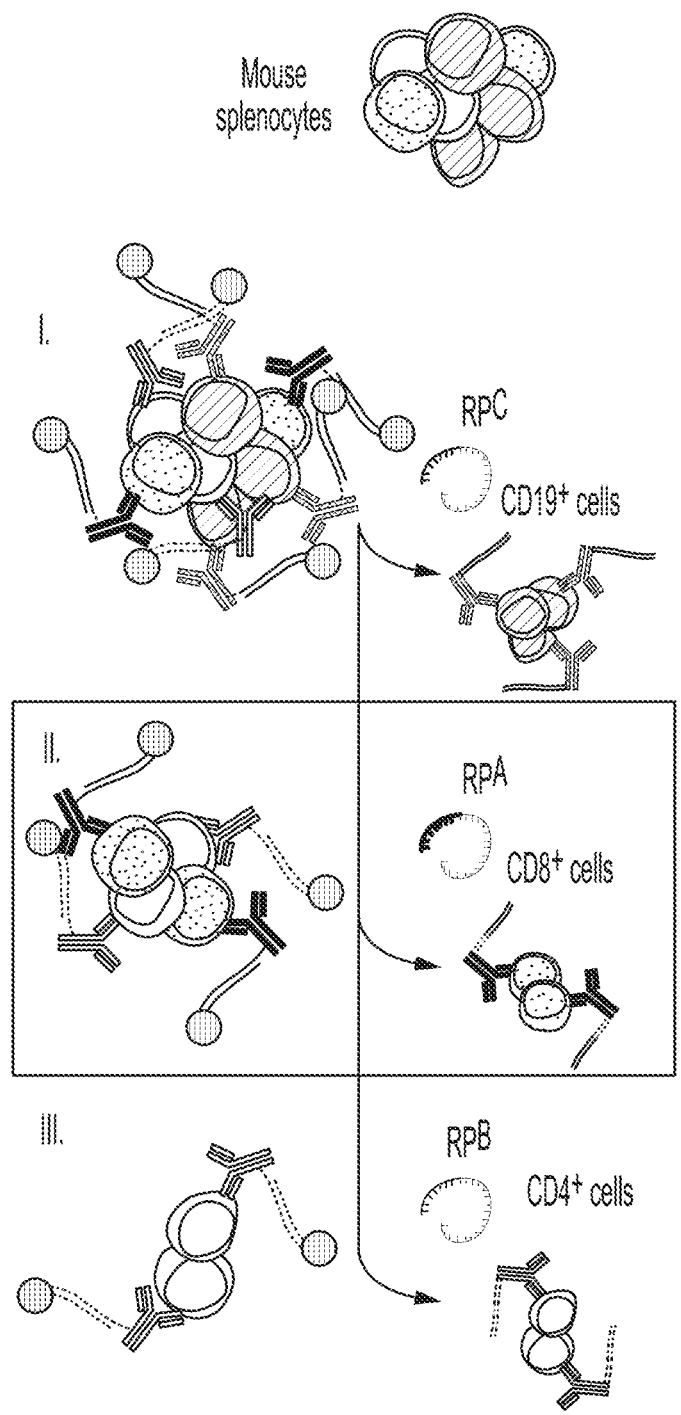
FIG. 6A is a schematic showing the workflow of multiplexed cell sorting of major immune cell types from murine splenocytes. Briefly, mouse splenocytes are isolated from C57BL/6J mice and the cell frequencies of B220+, CD8+, and CD4+ are determined. Next, splenocytes were magnetically labeled with DNA-gated antibodies targeting CD19 (Step I), CD8 (Step II), and CD4 (Step III). Individual populations were sequentially recovered by addition of appropriate RP strands.
Figures 6H, 6I, 6J:
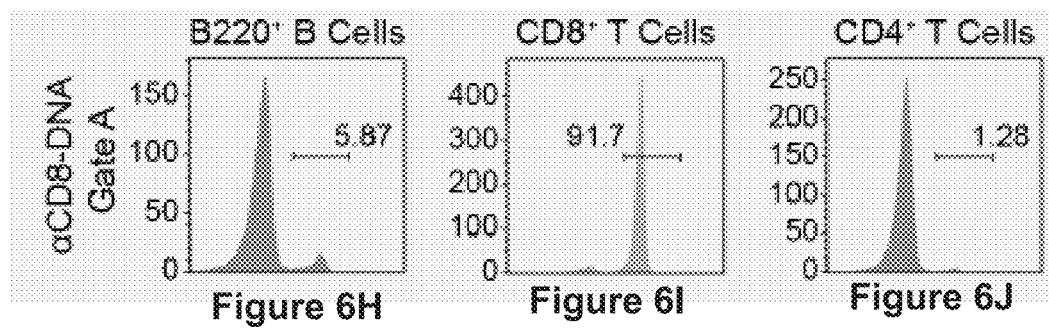
FIGS. 6H-6J are graphs showing the frequency of CD8-labeled B220+ (FIG. 6H), CD8+ (FIG. 6I), and CD4+ (FIG. 6J) splenocytes.
Figures 6K, 6L, 6M:
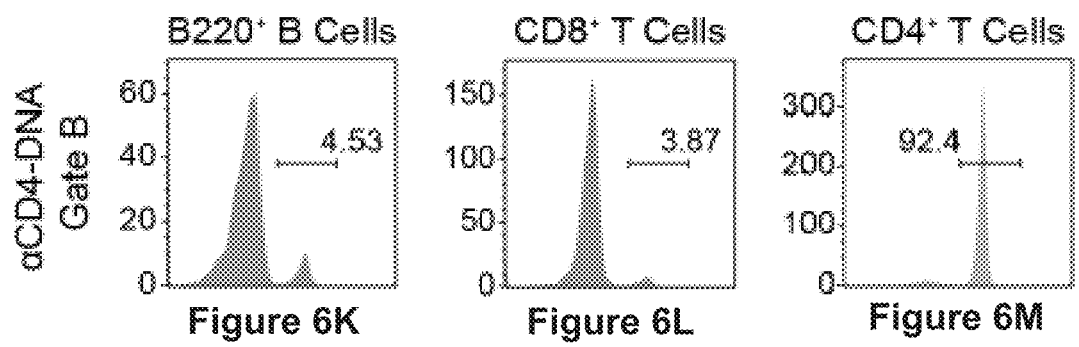
FIGS. 6K-6M are graphs showing the frequency of CD4-labeled B220+ (FIG. 6K), CD8+ (FIG. 6L), and CD4+ (FIG. 6M) splenocytes.

In contrast to standard bead-based sorting which lacks the ability to isolate multiple cell populations simultaneously, DGS is theoretically not limited in the number of cell types it can isolate from a sample because cell sorting is based on the orthogonality of DNA gates, and the number of all possible DNA sequences from which we can build orthogonal DNA strand displacement reactions scales exponentially with sequence length ($4^N$) To demonstrate the potential for parallel sorting by DGS, the disclosed panel of orthogonal DNA-gated antibodies were used for multiplexed sorting of primary CD19+ B cells, CD8+ T cells, and CD4+ T cells from mouse splenocytes. Splenocytes were harvested from C57BL/6J mice and initial CD19+, CD8+, and CD4+ immune cell frequencies were measured (FIGS. 6B-6D) before simultaneously staining cells with anti-mouse CD8-$TP^A$, anti-mouse CD4-$TP^B$, and anti-mouse CD19-$TP^C$.

Results

After annealing CP-coated magnetic beads to target cells for magnetic capture, the sequential addition of RP strands from each DNA gate resulted in recovery of specific target cell populations. The purity of each cell fraction was verified by staining for B220, CD8, and CD4 cell surface markers, finding that target cell purity after each displacement was >90% (FIGS. 6E-6M). B220 was used as a proxy for CD19 expression because binding of the DNA-gated antibody blocked staining of an alternate CD19 antibody clone used to measure frequency. It was confirmed that CD19 and B220 are co-expressed on B cells by co-staining (FIG. 7A-7D).

Figure 6N:
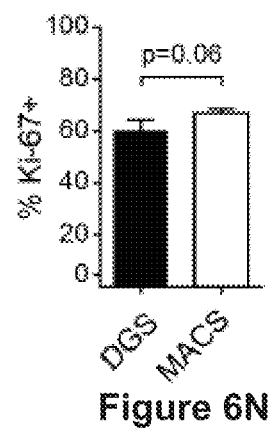
FIG. 6N is a bar graph showing proliferative potential of released CD8+ cells (DGS) compared to MACS sorted CD8+ cells (MACS).
Figure 6O:
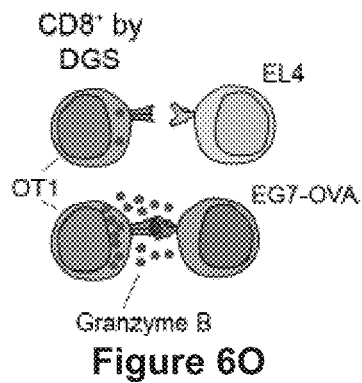
FIG. 6O is a schematic showing CD8+ cells purified by DGS from OT1 mice being co-incubated with EG7-OVA target cells and EL4 control cells.
Figures 7A, 7B, 7C, 7D:
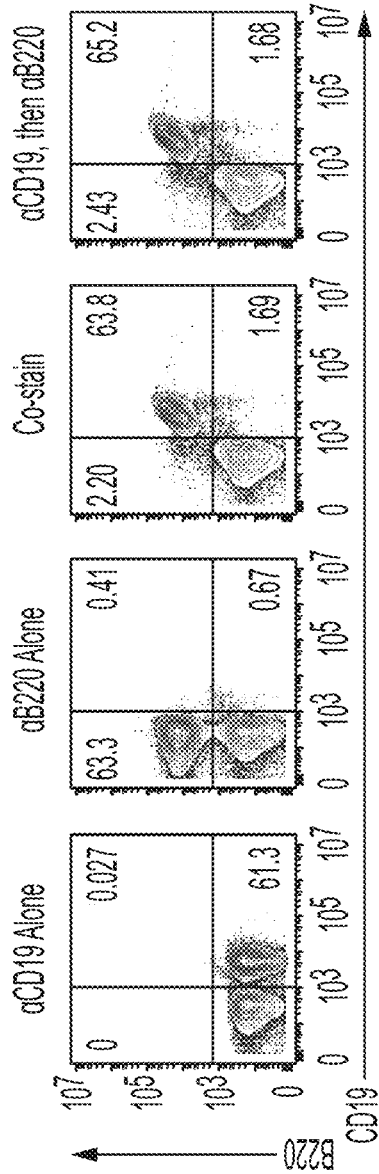
FIGS. 7A-7D are flow plots showing B220 and CD19 cell frequency in cells stained with αCD19 alone (FIG. 7A), αB220 alone (FIG. 7B), co-stain with αCD19 and αB220 (FIG. 7C), or cells stained with αCD19 and then αB220 (FIG. 7D).
Figures 8A, 8B, 8C:
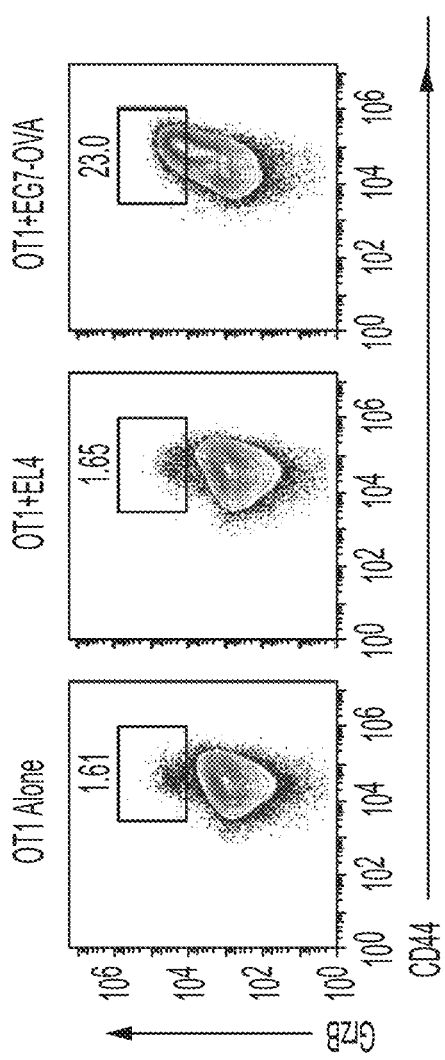
FIG. 8A-8C are flow plots showing granzyme B production in CD8+ cells sorted from OT1 mice (FIG. 8A), co-incubated with either OT-1+EL4 (FIG. 8B) or OT1+ EG7-OVA (FIG. 8C).

To confirm that cells remain functional after sorting by DNA-gated antibodies, T cell proliferation and killing markers were examined. DGS and MACS sorted CD8+ T cells were plate-activated using anti-mouse CD3/CD28 and stained for the proliferation marker K1-67 five days after sorting. 60.2% of DGS sorted cells exhibited proliferative capacity, equivalent to that of MACS sorted cells (DGS: 60.2% vs. MACS: 67.0%, p=0.06 by unpaired t test, n=3) (FIG. 6N). Additionally, an in vitro killing assay was performed. DGS sorted CD8+ T cells from transgenic OT1 mice, which express a T cell receptor specific for OVA257-264 antigen, were co-incubated with either EL4 (non-OVA expressing) controls or EG7-OVA (OVA-expressing) target cells and measured effector Granzyme B expression (FIG. 6O). A 15-fold increase in the number of CD8+ T cells expressing Granzyme B was observed when incubated with EG7-OVA cells compared to EL4 cells, consistent with the Granzyme B elevation seen in MACS sorted cells cultured with EG7-OVA cells (FIGS. 6P-6Q, FIGS. 8A-8C). These results show that multiplexed DGS enriches populations of several cell types from a single biological tissue to a high purity while preserving cellular function.

Example 4. Dual Gated DGS Isolates Antigen-Specific CD8+ T Cells

Methods and Materials

To expand DGS to dual gated sorting of cells expressing multiple markers, the use of DNA gates was extended to peptide-MHC tetramers for isolation of antigen-specific CD8+ T cells. DNA-gated pMHC tetramers were synthesized by expressing recombinant streptavidin engineered with a C-terminal cysteine residue (StvC) (Kwong, G A, et al., *J Am Chem Soc*, 131:9695-9703 (2009); Reznik, G O, et al., *Bioconjug Chem*, 12:1000-1004 (2001)) to site-specifically attach DNA at a location that would not impair binding of biotinylated pMHC monomers.

Results

Figures 9H, 9I, 9J:
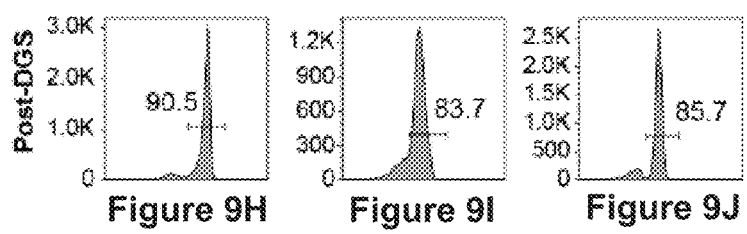
FIG. 9H-9J show the frequency of CD8+ (FIG. 9H), p14+ (FIG. 9I) and pmel+ (FIG. 9J) splenocytes after sorting by antibody and tetramer DGS from a mixture of B6, P14, and pmel splenocytes from P14 using a double positive gating scheme.
Figure 10A:
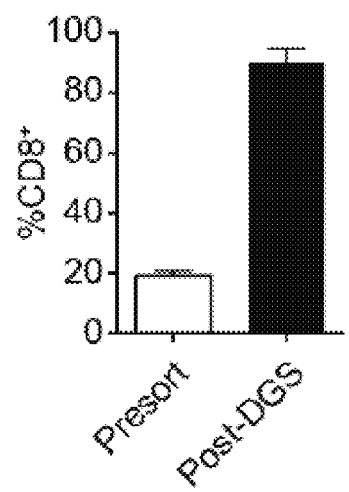
FIGS. 10A-10C are bar graphs showing the percent of CD8+ (FIG. 10A), P14-Tet+ (FIG. 10B), and pmel-Tet+ (FIG. 0C) cells in isolated cells from dual gated DGS using anti-mouse CD8 and pMHC tetramers in combination.
Figure 10B:
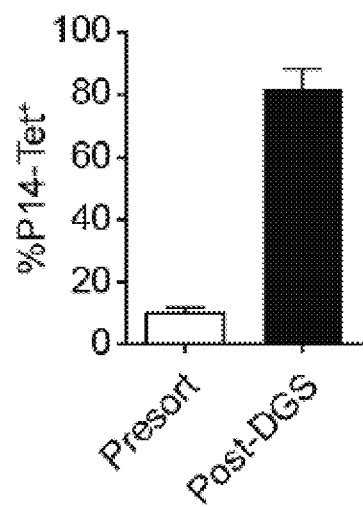
Figure 10C:
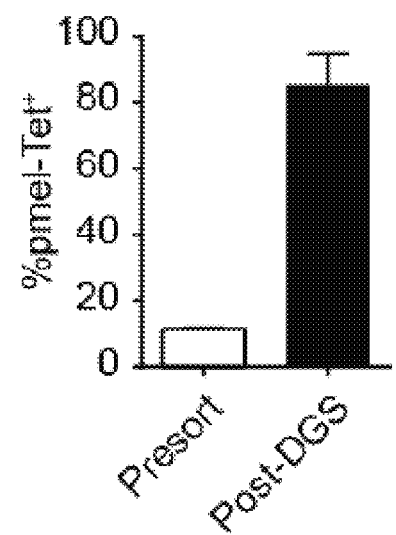

Efficient DNA strand displacement on TCR transgenic P14 or pmel T cells within whole splenocytes was confirmed using their respective pMHC tetramers (Db-GP33 or Db-GP100) (FIGS. 9A-9C). In a dual gated system designed to sort CD8+Tet+ cells, anti-mouse CD8-Gate A, Tet-Db-GP33-Gate B, and Tet-Db-GP100-Gate C was combined with a mixture of P14 and pmel splenocytes. CD8+ T cells were isolated in bulk to similar purities as in the single marker sort by addition of $RP^A$. From the CD8+ enriched subpopulation, P14 and pmel CD8+ T cells were eluted into two distinct samples by unlocking Gates B and C with $RP^B$ and $RP^C$ (FIGS. 9D-9J). To validate the composition of recovered cells, isolated cells were stained with fluorescent pMHC tetramer and observed enrichment to high purity for both P14 and pmel splenocytes (FIGS. 10A-10C).

Figure 9K:
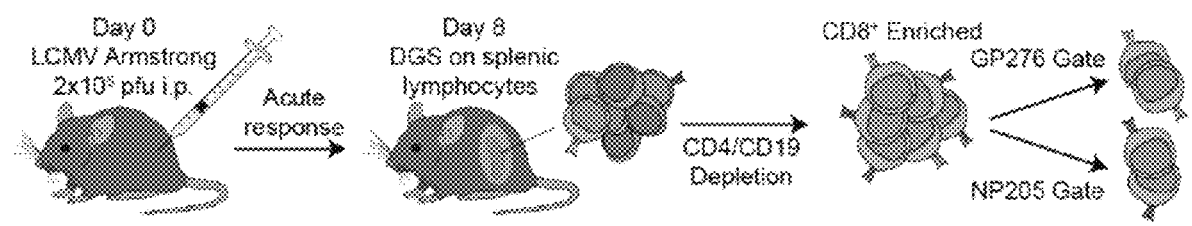
FIG. 9K is a schematic showing the experimental design for FIGS. 9L-9R. Briefly, C57BL/6J mice were injected i.p. with 2×10$^5$ pfu of LCMV Armstrong, and LCMV-specific CD8+ T cells were isolated at day 8 post-infection using antibody DGS to deplete CD4+ and CD19+ cells, followed by tetramer DGS to isolate LCMV-derived GP276- or NP205-specific populations.
Figure 9R:
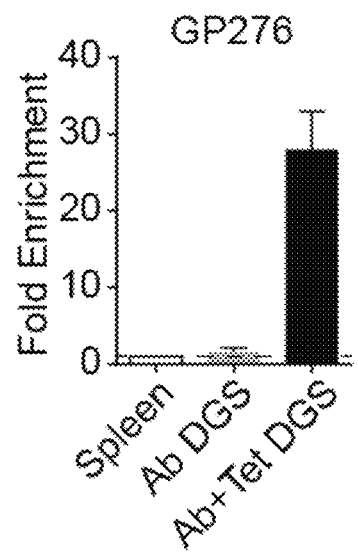
Figure 9S:
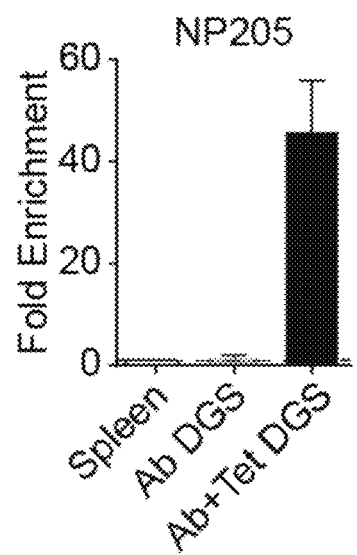

Dual gated tetramer sorting was applied to isolate antigen-specific T cells during an endogenous polyclonal immune response to infection using the model virus LCMV (FIG. 9K). During acute clearance (8 days p.i.), CD8+ T cells from the spleen specific for the known LCMV-derived antigens GP276 and NP205 were analyzed by tetramer staining (FIGS. 9L-9R). To sort GP276- and NP205-specific CD8+ T cells, CD8+ T cells from the spleen were enriched in bulk using negative selection by depleting CD4+ and CD19+ cells with DGS. No change in the frequency of tetramer-positive cells within the CD8+ population post-depletion was observed (FIGS. 11A-11H). Antigen-specific CD8+ T cells were isolated from the CD8 enriched sample by addition of RP strands to recover putative LCMV-specific populations. To validate the specificity of tetramer DGS, sorted samples were stained with allele matched control tetramers (Db-GP100 for Db-GP33 and Kb-OVA for Kb-NP205) and observed no binding (FIGS. 9L-9R). By contrast, staining with fluorescent tetramers used for DGS showed that both GP276 and NP205-specific populations were sorted to high purity and enriched ~30-50 fold from the spleen (FIGS. 9O, 9S). These results show that multiplexed DGS can be extended to complex targeting ligands and dual gating strategies to isolate cells based on expression of multiple surface markers.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A probe for cell sorting comprising:
   i) a single-stranded nucleic acid targeting probe comprising a toehold domain and a hybridization domain, wherein the toehold domain is conjugated to a binding moiety through a 5' end of the toehold and is conjugated or linked to the hybridization domain by a 3' end of the toehold, wherein the toehold domain comprises 30-70% guanine cytosine (GC) content; and
   ii) a complementary nucleic acid catch probe; wherein the nucleic acid catch probe is annealed to the hybridization domain of the nucleic acid targeting probe, and wherein the nucleic acid catch probe comprises a magnetic bead.

2. The probe for cell sorting of claim 1, wherein the toehold comprises 3 to 10 nucleotides.

3. The probe for cell sorting of claim 1, wherein the single-stranded targeting probe comprises 3 to 30 nucleotides.

4. The probe for cell sorting of claim 1, wherein the binding moiety comprises an antibody or antigen binding fragment thereof, a fusion protein, an aptamer, peptide major histocompatibility complex (MHC), multivalent construct containing peptide MHC, or a ligand for a cell surface receptor or cell surface protein.

5. The probe for cell sorting of claim 1, wherein the binding moiety specifically binds to a cell surface protein or a cell surface receptor.

6. The probe for cell sorting of claim 1, wherein the magnetic bead is conjugated to the catch probe by a biotin-streptavidin interaction.

7. A cell comprising the probe for cell sorting of claim 1 wherein the probe is bound to the surface of said cell.

8. The probe for cell sorting of claim 1, wherein the probe can sort cells selected from a group consisting of immune cells, cells genetically engineered to express a cell surface protein or cell surface receptor that binds at least one probe for cell sorting, or cancer cells.

9. The probe for cell sorting of claim 1, wherein the binding moiety comprises a peptide major histocompatibility complex (MHC) complex that targets T cell receptors unique for different antigen-specific T cells.

10. The probe for cell sorting of claim 1, wherein the binding moiety binds a peptide major histocompatibility complex (MHC) complex.

11. A kit comprising:
one or more probes for cell sorting according to claim 1, and
one or more release probes, wherein the release probes comprise a single-stranded nucleic acid probe having a complementary sequence to the targeting probe of the one or more probes for cell sorting.

12. The kit of claim 11, wherein the binding moiety of the cell sorting probe comprises an antibody or antigen binding fragment thereof, a fusion protein, an aptamer, peptide MHC complex, multivalent construct containing peptide MHC, or a ligand for a cell surface receptor or cell surface protein.

13. The kit of claim 11, wherein the binding moiety of the cell sorting probe specifically binds to a cell surface protein or a cell surface receptor.

14. The kit of claim 1, further comprising magnetic sorting buffers.

* * * * *